(12) United States Patent
Fachinger et al.

(10) Patent No.: US 9,132,186 B2
(45) Date of Patent: *Sep. 15, 2015

(54) REDUCTION OF CONCOMITANT INFECTIONS IN PIGS BY THE USE OF PCV2 ANTIGEN

(71) Applicants: Vicky Fachinger, Bad Soden (DE);
Knut Elbers, Mittelbiberach (DE);
Marion Kixmoeller, Munich (DE)

(72) Inventors: Vicky Fachinger, Bad Soden (DE);
Knut Elbers, Mittelbiberach (DE);
Marion Kixmoeller, Munich (DE)

(73) Assignee: Boehringer Ingelheim Vetmedica, Inc., St. Joseph, MO (US)

( * ) Notice: Subject to any disclaimer, the term of this patent is extended or adjusted under 35 U.S.C. 154(b) by 29 days.

This patent is subject to a terminal disclaimer.

(21) Appl. No.: 13/908,766

(22) Filed: Jun. 3, 2013

(65) Prior Publication Data

US 2013/0302370 A1    Nov. 14, 2013

Related U.S. Application Data

(63) Continuation of application No. 12/941,836, filed on Nov. 8, 2010, now Pat. No. 8,475,805, which is a continuation of application No. 12/198,721, filed on Aug. 26, 2008, now Pat. No. 7,829,274.

(30) Foreign Application Priority Data

Sep. 4, 2007 (EP) ..................................... 07115609

(51) Int. Cl.
*A61K 39/12* (2006.01)
*A61K 45/06* (2006.01)
*A61K 39/00* (2006.01)

(52) U.S. Cl.
CPC ................. *A61K 39/12* (2013.01); *A61K 45/06* (2013.01); *A61K 2039/552* (2013.01); *C12N 2750/10034* (2013.01)

(58) Field of Classification Search
None
See application file for complete search history.

(56) References Cited

U.S. PATENT DOCUMENTS

| | | | |
|---|---|---|---|
| 5,202,430 A | 4/1993 | Brian et al. |
| 5,322,774 A | 6/1994 | Peakman et al. |
| 5,436,001 A | 7/1995 | Kramer |
| 5,565,205 A | 10/1996 | Petersen et al. |
| 5,580,557 A | 12/1996 | Kramer |
| 5,733,555 A | 3/1998 | Chu |
| 5,885,823 A | 3/1999 | Knittel et al. |
| 5,925,359 A | 7/1999 | Van Woensel et al. |
| 5,968,525 A | 10/1999 | Fitzgerald et al. |
| 6,217,883 B1 | 4/2001 | Allan et al. |
| 6,287,856 B1 | 9/2001 | Poet et al. |
| 6,294,176 B1 | 9/2001 | Cochran et al. |
| 6,368,601 B1 | 4/2002 | Allan et al. |
| 6,391,314 B1 | 5/2002 | Allan et al. |
| 6,497,883 B1 | 12/2002 | Bublot et al. |
| 6,517,843 B1 | 2/2003 | Ellis et al. |
| 6,660,272 B2 | 12/2003 | Allan et al. |
| 6,703,023 B1 | 3/2004 | Jestin et al. |
| 6,794,163 B2 | 9/2004 | Liu et al. |
| 6,808,900 B2 | 10/2004 | Simonsen |
| 6,841,364 B2 | 1/2005 | Yuan et al. |
| 6,846,477 B2 | 1/2005 | Keich et al. |
| 6,943,152 B1 | 9/2005 | Audonnet et al. |
| 6,953,581 B2 | 10/2005 | Allan et al. |
| 7,018,638 B2 | 3/2006 | Chu et al. |
| 7,109,025 B1 | 9/2006 | Eloit et al. |
| 7,122,192 B2 | 10/2006 | Allan et al. |
| 7,144,698 B2 | 12/2006 | Wang et al. |
| 7,148,015 B2 | 12/2006 | Jestin et al. |
| 7,169,394 B2 | 1/2007 | Chu et al. |
| 7,172,899 B2 | 2/2007 | Liu et al. |
| 7,179,472 B2 | 2/2007 | Jestin et al. |
| 7,192,594 B2 | 3/2007 | Haines et al. |
| 7,211,379 B2 | 5/2007 | Ellis et al. |
| 7,223,407 B2 | 5/2007 | Jestin et al. |
| 7,223,594 B2 | 5/2007 | Jestin et al. |
| 7,244,433 B2 | 7/2007 | Jestin et al. |
| 7,258,865 B2 | 8/2007 | Jestin et al. |
| 7,261,898 B2 | 8/2007 | Jestin et al. |
| 7,273,617 B2 | 9/2007 | Yuan et al. |
| 7,276,353 B2 | 10/2007 | Meng et al. |
| 7,279,166 B2 | 10/2007 | Meng et al. |
| 7,297,537 B2 | 11/2007 | Jestin et al. |
| 7,300,785 B2 | 11/2007 | Meerts et al. |

(Continued)

FOREIGN PATENT DOCUMENTS

| | | |
|---|---|---|
| CA | 2305623 A1 | 4/1999 |
| CN | 1579553 A | 7/1920 |

(Continued)

OTHER PUBLICATIONS

Mahe et al. (Journal of General Virology. 2000; 81: 1815-1824).*

(Continued)

*Primary Examiner* — Shanon A Foley

(74) *Attorney, Agent, or Firm* — Michael P. Morris; Wendy M. Gombert

(57) ABSTRACT

The present invention relates to a method for reducing the percentage of concomitant infections in pigs or a herd of pigs caused by pathogens other than PCV2 comprising the step administering to said pig(s) an effective amount of PCV2 antigen or an immunogenic composition comprising PCV2 antigen. It also refers to a method for improving the resistance of pigs against concomitant infections with pathogens other than PCV2, comprising the step administering to said pig(s) an effective amount of PCV2 antigen or an immunogenic composition comprising PCV2 antigen.

4 Claims, 1 Drawing Sheet

(56) References Cited

U.S. PATENT DOCUMENTS

| | | |
|---|---|---|
| 7,312,065 B2 | 12/2007 | Roof et al. |
| 7,314,628 B2 | 1/2008 | Jestin et al. |
| 7,323,330 B2 | 1/2008 | Jestin et al. |
| 7,335,361 B2 | 2/2008 | Liao et al. |
| 7,358,075 B2 | 4/2008 | Allibert et al. |
| 7,368,117 B2 | 5/2008 | Fetzer et al. |
| 7,371,395 B2 | 5/2008 | Parisot et al. |
| 7,390,494 B2 | 6/2008 | Jestin et al. |
| 7,405,075 B2 | 7/2008 | Jestin et al. |
| 7,407,803 B2 | 8/2008 | Jestin et al. |
| 7,425,444 B2 | 9/2008 | Jestin et al. |
| 7,700,285 B1 | 4/2010 | Eichmeyer et al. |
| 7,758,865 B2 | 7/2010 | Jestin et al. |
| 7,829,101 B2 * | 11/2010 | Eichmeyer et al. ........ 424/204.1 |
| 7,829,273 B2 * | 11/2010 | Roof et al. .................. 435/5 |
| 7,829,274 B2 * | 11/2010 | Fachinger et al. ............ 435/5 |
| 7,833,707 B2 | 11/2010 | Eichmeyer et al. |
| 7,838,213 B2 * | 11/2010 | Roof et al. .................. 435/5 |
| 7,838,214 B2 | 11/2010 | Roof et al. |
| 7,910,306 B2 | 3/2011 | Eichmeyer et al. |
| 7,914,992 B2 * | 3/2011 | Fachinger et al. ............ 514/3.7 |
| 7,943,298 B2 | 5/2011 | Fachinger et al. |
| 7,951,907 B2 | 5/2011 | Jestin et al. |
| 7,968,285 B2 | 6/2011 | Roof et al. |
| 8,025,888 B2 | 9/2011 | Eichmeyer et al. |
| 8,119,143 B2 * | 2/2012 | Roof et al. .................. 424/204.1 |
| 8,475,805 B2 * | 7/2013 | Fachinger et al. ........ 424/204.1 |
| 8,496,940 B2 | 7/2013 | Fachinger et al. |
| 8,852,613 B2 | 10/2014 | Ohnesorge et al. |
| 2002/0146431 A1 | 10/2002 | Allan et al. |
| 2003/0096377 A1 | 5/2003 | Meng et al. |
| 2003/0170270 A1 | 9/2003 | Meng et al. |
| 2003/0199581 A1 | 10/2003 | Seligson et al. |
| 2003/0215455 A1 | 11/2003 | Reynolds et al. |
| 2004/0062775 A1 | 4/2004 | Jestin et al. |
| 2004/0076635 A1 | 4/2004 | Jestin et al. |
| 2004/0091502 A1 | 5/2004 | Jestin et al. |
| 2004/0132178 A1 | 7/2004 | Haines et al. |
| 2004/0161410 A1 | 8/2004 | Jestin et al. |
| 2004/0208901 A1 | 10/2004 | Ellsworth et al. |
| 2004/0253270 A1 | 12/2004 | Meng et al. |
| 2004/0258715 A1 | 12/2004 | Allan et al. |
| 2004/0265848 A1 | 12/2004 | Jestin et al. |
| 2005/0008651 A1 | 1/2005 | Jestin et al. |
| 2005/0013823 A1 | 1/2005 | Keich et al. |
| 2005/0031647 A1 | 2/2005 | Roof et al. |
| 2005/0058653 A1 | 3/2005 | Ellis et al. |
| 2005/0079185 A1 | 4/2005 | Parisot et al. |
| 2005/0084497 A1 | 4/2005 | Jestin et al. |
| 2005/0147966 A1 | 7/2005 | Meng et al. |
| 2005/0238662 A1 | 10/2005 | Jestin et al. |
| 2006/0002952 A1 | 1/2006 | Haines et al. |
| 2006/0029617 A1 | 2/2006 | Charreyre et al. |
| 2006/0083756 A1 * | 4/2006 | Jestin et al. ................. 424/204.1 |
| 2006/0115489 A1 | 6/2006 | Birkett et al. |
| 2006/0204522 A1 | 9/2006 | Kroll et al. |
| 2006/0222659 A1 | 10/2006 | Jestin et al. |
| 2006/0228373 A1 | 10/2006 | Chu et al. |
| 2006/0233831 A1 | 10/2006 | Parisot et al. |
| 2006/0246425 A1 | 11/2006 | Allibert et al. |
| 2006/0286123 A1 | 12/2006 | Fetzer et al. |
| 2007/0196879 A1 | 8/2007 | Chabriere et al. |
| 2008/0181910 A1 | 7/2008 | Roof et al. |
| 2008/0226669 A1 | 9/2008 | Roof et al. |
| 2008/0233147 A1 | 9/2008 | Jestin et al. |
| 2008/0261887 A1 | 10/2008 | Roof et al. |
| 2008/0267995 A1 | 10/2008 | Roof et al. |
| 2008/0279875 A1 | 11/2008 | Roof et al. |
| 2008/0279876 A1 | 11/2008 | Roof et al. |
| 2008/0279889 A1 | 11/2008 | Roof et al. |
| 2009/0016992 A1 | 1/2009 | Eichmeyer et al. |
| 2009/0017064 A1 | 1/2009 | Wu et al. |
| 2009/0022751 A1 | 1/2009 | Eichmeyer et al. |
| 2009/0042245 A1 | 2/2009 | Eichmeyer et al. |
| 2010/0136060 A1 | 6/2010 | Kolb |
| 2010/0184016 A1 | 7/2010 | Lefebvre et al. |
| 2010/0189743 A1 | 7/2010 | Jestin et al. |
| 2011/0033495 A1 | 2/2011 | Roof et al. |
| 2011/0059126 A1 | 3/2011 | Kohler et al. |
| 2011/0091499 A1 | 4/2011 | Fachinger et al. |
| 2011/0217327 A1 | 9/2011 | Roof et al. |
| 2011/0274710 A1 | 11/2011 | Eichmeyer et al. |
| 2013/0115236 A1 | 5/2013 | Fachinger et al. |
| 2013/0230558 A1 | 9/2013 | Ohnesorge et al. |
| 2013/0273099 A1 | 10/2013 | Fachinger et al. |
| 2013/0302370 A1 * | 11/2013 | Fachinger et al. ......... 424/204.1 |

FOREIGN PATENT DOCUMENTS

| | | |
|---|---|---|
| CN | 1458167 A | 11/2003 |
| CN | 103122352 A | 5/2013 |
| EP | 1050584 A1 | 11/2000 |
| EP | 1281760 A1 | 2/2003 |
| EP | 1386617 A1 | 2/2004 |
| JP | 2002247979 A | 9/2002 |
| JP | 2005511075 A | 4/2005 |
| WO | 8906972 A1 | 8/1989 |
| WO | 9007935 A1 | 7/1990 |
| WO | 9118627 A1 | 12/1991 |
| WO | 9203157 A1 | 3/1992 |
| WO | 9316726 A2 | 9/1993 |
| WO | 9636356 A1 | 11/1996 |
| WO | 9918214 A1 | 4/1999 |
| WO | 9929717 A3 | 6/1999 |
| WO | 9929871 A3 | 6/1999 |
| WO | 0001409 A2 | 1/2000 |
| WO | 0047756 A1 | 8/2000 |
| WO | 0077188 A2 | 12/2000 |
| WO | 0077216 A2 | 12/2000 |
| WO | 0116330 A2 | 3/2001 |
| WO | 0117556 A1 | 3/2001 |
| WO | 0134191 A1 | 5/2001 |
| WO | 0145735 A2 | 6/2001 |
| WO | 0196377 A2 | 12/2001 |
| WO | 0249666 A2 | 6/2002 |
| WO | 02077210 A2 | 10/2002 |
| WO | 03003941 A2 | 1/2003 |
| WO | 03049703 A2 | 6/2003 |
| WO | 2004026336 A1 | 4/2004 |
| WO | 2004058142 A2 | 7/2004 |
| WO | 2004069184 A2 | 8/2004 |
| WO | 2005009462 A2 | 2/2005 |
| WO | 2005092069 A2 | 10/2005 |
| WO | 2005112995 A1 | 12/2005 |
| WO | 2006068663 A2 | 6/2006 |
| WO | 2006072065 A2 | 7/2006 |
| WO | 2006113372 A2 | 10/2006 |
| WO | 2006113373 A2 | 10/2006 |
| WO | 2007028823 A1 | 3/2007 |
| WO | 2007076520 A2 | 7/2007 |
| WO | 2007094893 A2 | 8/2007 |
| WO | 2008073464 A2 | 6/2008 |
| WO | 2008076915 A2 | 6/2008 |
| WO | 2008081015 A1 | 7/2008 |
| WO | 2008098909 A1 | 8/2008 |
| WO | 2009030684 A2 | 3/2009 |
| WO | 2009103037 A1 | 8/2009 |
| WO | 2011116094 A2 | 9/2011 |
| WO | 2014134561 A2 | 9/2014 |

OTHER PUBLICATIONS

Duarte et al. (Acta Scientiae Veterinariae. 2013; 41 (Suppl 1): 37.*
Takada-Iwao et al. (Veterinary Microbiology. 2013; 162: 219-223).*
Opriessnig et al. (Veterinary Microbiology. 2008; 131: 103-114).*
Kixmoller et al. (Vaccine. 2008; 26: 3443-3451).*
Zhang et al. (Veterinary Immunology and Immunopathology. 2011; 140: 152-158).*
Ladekjaer-Mikkelsen et al., "Reproduction of postweaning multisystemic wasting syndrome (PMWS) in immunostimulated and non-immunostimulated 3-week-old piglets experimentally infected with prcine circovirus type 2 (PCV2)". 2002, Veterinary Microbiology, vol. 89, pp. 97-114.

(56) References Cited

OTHER PUBLICATIONS

Liu et al., "Bacterial Expression of an Immunologically Reactive PCV2 ORF2 Fusion Protein". 2001, Protein Expression and Purification, vol. 21, pp. 115-120.
Liu et al., "Characterization of a Previously Unidentified Viral Protein in Porcine Circovirus Type 2-Infected Cells and Its Role in Virus-Induced Apoptosis". Jul. 2005, Journal of Virology, vol. 79, No. 13, pp. 8262-8274.
Mackinnon, J.D., "Vaccination Ramification? An Objective Look at How Vaccination Might Affect Post-Weaning Multisystemic Wasting Syndrome (PMWS) and Porcine Dermatitis and Nephropathy Syndrome (PDNS)". 2003, The Pig Journal, vol. 51, pp. 36-63.
Maes et al., "Effect of vaccination against *Mycoplasma hyopneumoniae* in pig herds with an all-in/all-out production system". Vaccine, vol. 17, 1999, pp. 1024-1034.
Mahe et al., "Differential recognition of ORF2 protein from type 1 and type 2 porcine circoviruses and identification of immunorelevant epitopes". 2000, Journal of General virology, vol. 81, pp. 1815-1824.
Maranga et al., "Virus-Like Particle Production at Low Multiplicities of Infection With the Baculovirus Insect Cell System". Aug. 2003, Biotechnology and Bioengineering, vol. 84, No. 2, pp. 246-253.
McNeilly et al., "Evaluation of a Porcine Circovirus Type 2-Specific Antigen-Captive Enzyme-Linked Immunosorbent Assay for the Diagnosis of Postweaning Multisystemic Wasting Syndrome in Pigs: Comparison with Virus Isolation, Immunohistochemistry, and the Polymerase Chain Reaction", J. Vet Diagn. Invest, 2002, 14, pp. 106-112.
Minion et al., "Then Genome Sequence of *Mycoplasma hyopneumoniae* Strain 232, the Agent of Swine Mycoplasmosis". Nov. 2004, Journal of Bacteriology, vol. 186, No. 21, pp. 7123-7133.
Morales et al., "Serendipitous Discovery and X-Ray Structure of a Human Phosphate Binding Apolipoprotein". Mar. 2006, Structure, vol. 14, pp. 601-609.
Morris et al., "Characterization of Productive and Non-Productive ACMNPV Infection in Selected Insect Cell Lines", Viro. 197, 1993, pp. 339-348.
Morris et al., "Promoter Influence on Baculovirus-Mediated Gene jExpression in Permissive and Nonpermissive Insect Cell Lines", J. Virol., Dec. 1992, vol. 66, No. 12, pp. 7397-7405.
Nawagitgul et al., "Open reading frame 2 of porcine circovirus type 2 encodes a major capsid protein". 2000, Journal of General Virology, vol. 81, pp. 2281-2287.
Nawagitgul et al., Modified Indirect Porcine Circovirus (PCV) Type 2-based and Recombinant Capsid Protein (ORF-2) Based Enzyme-Linked Immunosorbent Assays for Detection of Antibodies to PCV, Clinical and Diagnostic Laboratory Imunology, Ja. 2002, vol. 9, No. 1, pp. 33-40.
Okuda, et al., "Experimental Reproduction of Post-Weaning Multisystemic Wasting Syndrome in Cesarean-Derived, Colostrum-Deprived Piglets Inoculated with Porcine Circovirus Type 2 (PCV2): Investigation of Quantitative PCV2 Distribution and Antibody Responses", J. Vet Diagn. Invest, 2003, 15, pp. 107-114.
Olvera et al., "Comparison of porcine circovirus type 2 load in serum quantified by a real time PCR in postweaning multisystemic wasting syndrome and porcine dermatitis and nephropathy syndrome naturally affected pigs". 2004, Journa of Virological Methods, vol. 117, pp. 75-80.
Opriessnig et al., "Derivation of porcine circovirus type 2-negative pigs from positive breeding herds". Journal of Swine Health and Production, vol. 12, No. 4, Jul. and Aug. 2004, pp. 186-191.
Opriessnig et al., "Experimental Reproduction of Postweaning Multisystemic Wasting Syndrome in Pigs by Dual Infection with *Mycoplasma hyopneumoniae* and Porcine Circovirus Type 2". Veterinary Pathology, vol. 41, No. 6, Nov. 2004, pp. 624-640.
Opriessnig et al., "Porcine Circovirus Type 2 Infection Decreases the Efficacy of a Modified Live Porcine Reproductive and Respiratory Syndrome Virus Vaccine", Clinical and Vaccine Immunology, Aug. 2006, vol. 13, No. 8, pp. 923-929.

Ostanello et al., "Experimental infection of 3-week-old conventional colostrum-fed pigs with porcine circovirus type 2 and porcine parvovirus". Veterinary Microbiology, vol. 108, No. 3-4, Jul. 2008, pp. 179-186.
Quintana et al., "Clinical and pathological observations on pigs with postweaning multisystemic wasting syndrome". 2001, The Veterinary Record, vol. 149, pp. 357-361.
Riggs et al., "Protective Monoclonal Antibody Defines a Circumsporozoite-Like Glycoprotein Exoantigen of *Cryptosporidium parvum* Sporozoites and Merozoites". The Journal of Immunology, vol. 158, 1997, pp. 1787-1795.
Rovira et al., "Experimental Inoculation of Conventional Pigs with Porcine Reproductive and Respiratory Syndrome virus and Porcine Circovirus 2", J. Virol, Apr. 2002, vol. 76, No. 7, pp. 3232-3239.
Royer et al., "Susceptibility of porcine circovirus type 2 to commercial and laboratory disinfectants". Journal of Swine Health and Production, vol. 9, No. 6, 2001, pp. 281-284.
Rueda et al., "Effect of Different Baculovirus Inactivation Procedures on the Integrity and Immunogenicity of Porcine Parvovirus-Like Particles", Vaccine, 2001, 19, pp. 726-734.
Segales et al., "Changes in Peripheral Blood Leukocyte Populations in Pigs with Natural Postweaning Multisystemic Wasting Syndrome (PMWS)", Vet. Immunology & Immunopathology, 2001, 81, pp. 37-44.
Segales et al., "Epidemiology of Porcine Circovirus Type 2 Infection: What do we Know?", Pig News & Information, 2003, vol. 24, No. 4, pp. 103N-110N.
Segales et al., "Granulomatous Enteritis and Lymphadenitis in Iberian Pigs Naturally Infected with *Lawsonia intracellularis*". Veterinary Pathology, vol. 38, No. 3, 2001, pp. 343-346.
Segales et al., "Postweaning Multisystemic Wasting Syndrome (PMWS) in Pigs, A Review", Vet. Quarterly, 2002, 24 (3), pp. 109-124.
Sequence alignment of SEQ ID No. 11 with UniProt database accession No. 091862 of Meehan et al., entered Nov. 1, 1998.
Sibila et al., "Use of a Polymerase Chain Reaction Assay and ELISA to Monitor Porcine Circovirus Type 2 Infection in Pigs From Farms with and without Postweaning Multisystemic Wasting jSyndrome", AJVR, Jan. 2004, vol. 65, No. 1, pp. 88-92.
Sorden et al., "Development of a Polyclonal-antibody-based Immunohystochemical Method for the Detection of Type 2 Porcine circovirus in Formalin-Fixed, Paraffin-Embedded Tissue", J. Vet Diagn. Inest, 1999, 11, pp. 528-530.
Thacker, Eileen L., "Mycoplasmal Diseases". Diseases of Swine, 9th Edition, Ch. 42, 2006, pp. 701-717.
Vansickle, J., "Circovirus Grips Industry". Jul. 15, 2006, National Hog Farmer.
Vasconcelos et al., "Swine and Poultry Pathogens: the Complete Genome Sequences of Two Strains of *Mycoplasma hyopneumoniae* and a Strain of *Mycoplasma synoviae*". Aug. 2005, Journal of Bacteriology, vol. 187, No. 16, pp. 5568-5577.
VIDO Swine Technical Group-Linking Knowledge to practical solutions "Vaccination Guidelines for Swine". Jun. 2004, www.vido.org.
Vincent et al., "Dendritic Cells Harbor Infetious Porcine Circovirus Type 2 in the Abscence of Apparent Cell Modulation or Replication of the Virus". Dec. 2003, Journal of Virology, vol. 77, No. 24, pp. 13288-13300.
Walker, et al., "Development and application of a competitive enzyme-linked immunosorbent assay for the detection of serum antibodies to porcine circovirus type 2". 2000, Journal of Veterinary Diagnostic Investigation, vol. 12, pp. 400-405.
WEB site: "Does stress-free livestock mean safer food?" http://www.foodnavigator.com/Financial-Industry/Does-stress-free-livestock-mean-safer-food Accessed on: Jun. 4, 2004.
Yang, "A Survey on Porcine Circovirus Type 2 Infection and Phylogenetic Analysis of its ORF2 Gene in Hangzhou, Zhejiang Province, CN," J. Zhejiang Univ. Science B, vol. 9(2), 2008, pp. 148-153.
Abstract in English of CN1458167, dated Nov. 26, 2003.
Albina et al., "An Experimental Model for Post-weaning Multisystenic Wasting Syndrome (PMWS) in Growing Piglets". 2001, Journal of Comparative Pathology, vol. 123, pp. 292-303.

(56) References Cited

OTHER PUBLICATIONS

Allan et al., "Experimental infection of colostrum deprived piglets with porcine circovirus 2 (PCV2) and procine reproductive and respiratory syndrome virus (PRRSV) potentiates PCV2 replication". 2000, Archives of Virology, vol. 145, pp. 2421-2429.
Allan et al., "Letters, Immunostiulations, PCV-2 and PMWS", The Vet. Records, Aug. 5, 2000, pp. 170-171.
Allan et al., "Passive Transfer of Maternal Antibodies to PCV2 Protects Against Development of Post-weaning Multisystemic Wasting Syndrome (PMWS): Experiemental Infections and a Field Study". 2002, The Pig Journal, vol. 50, pp. 59-67.
Allan et al., "PMWS/PCVD: Diagnosis, Disease, and Control: What do we know?" 2006, Proceedings of the 19th IPVS Congress, Copenhagen, Denmark, vol. 1, pp. 1-9.
Allan et al., "Porcine Circoviruses; A Review", J. Vet., Diagn. Invest. 2000, 12, pp. 3-14.
Allan et al., "Reproduction of postweaning multisystemic wasting syndrome in pigs experimentally inoculated with a Swedish porcine circovirus 2 isolate". 2003, Journal of Veterinary Diagnostic Investigation, vol. 15, pp. 553-560.
Allan et al., Guest Editorial, "PCV-2 Infection in Swine; More Than Just Postweaning Multisystemic Wasting Syndrome", The Vet Journ., 2003, 166, pp. 222-223.
Bassaganya-Riera et al., "Conjugated Linoleic Acid Ameliorates Viral Infectivity in a Pig Model of Virally Induced Immunosuppression". 2003, American Society for Nutritional Sciences, pp. 3204-3214.
Blanchard et al., "Protection of swine against post-weaning multisystemic wasting syndrome (PMWS) by porcine circovirus type 2 (PCV2) proteins". Vaccine, vol. 21, 2003, pp. 4565-4575.
Boehringer Ingelheim Vetmedica, Inc., "Data from studies consistent with maintaining safety and efficacy of Ingelvac CircoFLEXâ and Ingelvac MycoFLEXâ vaccines when mixed together and administered concurrently to pigs". Feb. 2008, Technical Bulletin, www.bi-vetmedica.com/swine-research/MycoFLEX-Mycoplasma-immunity_TB2.pdf; 14 pages.
Boehringer Ingelheim Vetmedica, Inc., Ingelvacâ Circoflexâ Material Safety Data Sheet, Online Oct. 2006, pp. 1-10, URL:http://bi-vetmedica.com/sites/default/files/ingelvac-circoflex-msds.pdf.
Boisseson et al., "Molecular characterization of Porcine circovirus type 2 isolates from post-weaning multisystemic wasting syndrome-affected and non-affected pigs". 2004, Journal of General Virology, vol. 85, pp. 293-304.
Bolin et al., "Postweaning multisystemic wasting syndrome induced after experimental inoculation of cesarean-derived, colostrum-deprived piglets with type 2 porcine circovirus". 2001, Journal of Veterinary Diagnostice Investigation, vol. 13, pp. 185-194.
Bowie, et al., "Deciphering the Message in Protein Sequences: Tolerance to Amino Acid Substitutions," Science, vol. 247, 1990, pp. 1306-1310.
Caprioli et al., "PCR detection of porcine circovirus type 2 (PCV2) DNA in blood, tonsillar and faecal swabs from experimentally infected pigs". Research in Veterinary Sciences, vol. 81, No. 2, Oct. 2006, pp. 287-292.
Chae, C. "A review of porcine circovirus 2-associated syndromes and diseases". The Veterinary Journal, vol. 169, No. 3, 2005, pp. 326-336.
Chae, C., "Postweaning multisystemic wasting syndrome: a review of aetiology, diagnosis and pathology". 2004, The Veterinary Journal, vol. 168, pp. 41-49.
Charbonneau, G., "Canadian Experiences with Porcine Circovirus Associated Disease". 2007, Iowa Pork Congress; 30 pages.
Chen et al., "Serological survey of serum antibodies against porcine circovirus type 2 (PCV2) in swine, chicken, duck, goat and cattle fromZhejiang province, China". Revue de Médecine Vétérinaire, vol. 158, Nos. 8-9, 2007, pp. 458-462.
Cheung et al., "Kinetics of Porcine Circovirus Type 2 Replication". Archives of Virology, vol. 147, 2002, pp. 43-58.
Chiou, et al., "The Effect of Porcine Circovirus Infection on the Immune Response of Pigs After Vaccination Against Classical Swine Fever and Pseudorabies". 2006, Proceedings of the 19th IPVS Congress, Copenhagen, Denmark, p. 79.
Czermak et al., "Membrane Filtration in Animal Cell Cutlure". 2007, Methods in Biotechnology, vol. 24, pp. 397-420, Humana Press, New Jersey, USA.
Darwich et al., "Cytokine profiles of peripheral blood mononuclear cells from pigs with postweaning multisystemic wasting syndrome in response to mitogen, superantigen or recall viral antigens". 2003, Journal of General Virology, vol. 84, pp. 3453-3457.
Dawson et al., "Studies of the field efficacy and safety of a single-dose *Mycoplasma hyopneumoniae* vaccine for pigs". Veterinary Record, vol. 151, 2002, pp. 535-538.
Ellis et al., "Lack of antibodies to porcine circovirus type 2 virus in beef and dairy cattle and horses in western Canada". Canadian Veterinary Journal, vol. 42, 2001, pp. 461-464.
Ellis et al., "Porcine circovirus-2 and concurrent infections in the field". Veterinary Microbiology, vol. 98, No. 2, Feb. 2004, pp. 159-163.
Fachinger et al., "The effect of vaccination against porcine circovirus type 2 in pigs suffering from porcine respiratory disease complex". 2008, Vaccine, vol. 26, pp. 1488-1499.
Fan et al., "Immunogenicity of Empty Capsids of Porcine Circovirus Type 2 Produced in Insect Cells". 2007, Veterinary Research Communications, vol. 31, pp. 487-496.
Fenaux et al., "A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Imunity Against PCV2 Infection in Pigs", J. Virol, Jun. 2004, vol. 78, No. 12, pp. 6297-6303.
Gagrcin et al., "Complex of Swine Respiratory Diseases—Strategy of control in light of latest knowledge". Veterinarski Glasnik, vol. 58, No. 7-8, 2004, pp. 409-418.
Genbank Accession No. AAC61738, Version AAC61738.1 GI:3661517, Sep. 29, 1998.
Genbank Accession# AAF87231, PCV2 ORF2 Protein, 2000.
Groner, et al., The Biology of Baculoviruses, vol. 1, Biological Properties and Moleculary Biology, 1986, Chapter 9, Specificity and Safety of Baculoviruses, pp. 177-202.
Ha et al., "Outbreak of salmonellosis in pigs with postweaning multisystemic wasting syndrome". Veterinary Record, vol. 156, No. 18, Apr. 2005, pp. 583-584.
International Search Report and Written Opinion for PCT/EP2008/061566 mailed on Jun. 18, 2009.
Inumaru et al., "Expression of biologically active recombinant porcinee GM-CSF by baculovirus gene expression system". 1998, Immunology and Cell Biology, vol. 76, pp. 195-201.
Jensen et al., "Distinction between Porcine Circovirus Type 2 Enteritis and Porcine Proliferative Enteropathy caused by *Lawsonia intracellularis*". Journal of Comparative Pathology, vol. 135, 2006, pp. 176-182.
Ju et al., "Immunogenicity of a recombinant pseudorabies virus expressing ORF1-ORF2 fusion protein of porcine circovirus type 2". 2005, Veterinary Microbiology, vol. 109, pp. 179-190.
Kamstrup, et al., "Immunisation against PCV2 structural protein by DNA vaccination of mice". 2004, Vaccine, vol. 22, pp. 1358-1361.
Kim et al., "A comparison of the Lymphocyte Subpopulations of Pigs Experimentally Infected with Porcine Circovirus 2 and/or Parvovirus". 2003, The Veterinary Journal, vol. 165, pp. 325-329.
Kim et al., "Association of Porcine Circovirus 2 with Porcine Respiratory Disese Complex", The Vet. Jour., 2003, 166, pp. 251-256.
Kim et al., "Characterization of the Recombinant Proteins of Porcine Circovirus Type2 Field Isolate Expressed in the Baculovirus System". 2002, Journal of Veterinary Science, vol. 3, No. 1, pp. 19-23.
Kim et al., "Efficacy of different disinfectants in vitro against porcine circovirus type 2". The Veterinary Record, vol. 164, May 2009, pp. 599-600.
Kim et al., "Enteritis associated with procine circovirus 2 in pigs". 2004, The Canadian Journal of Veterinary Research, vol. 68, pp. 218-221.
Kixmoller et al., "Reduction of PMWS-associated clinical signs and co-infections by vaccination against PCV2". 2008, Vaccine, vol. 26, pp. 3443-3451.

(56) References Cited

OTHER PUBLICATIONS

Kost, et al., "Recombinant baculoviruses as mammalian cell gene-delivery vectors". Apr. 2002, Trends in Biotechnology, vol. 20, No. 4, pp. 173-180.
Krakowka et al., "Features of porcine circovirus-2 disease: correlations between lesions, amount and distribution of virus, and clinical outcome". Journal of Veterinary Diagnostic Investigation, vol. 17, No. 3, May 2005, pp. 213-222.
Kyriakis et al., "The Effects of Immuno-modulation of the Clinical and Pathological Expression of Postweaning Multisystemic Wasting Syndrome". 2002, Journal of Comparative Pathology, vol. 126, pp. 38-46.
Fenaux et al., "Genetic Characterization of Type 2 Porcine Circovirus (PCV-2) from Pigs with Postweaning Multisystemic Wasting Syndrome in Different Geographic Regions of North America and Development of a Differential PCR-Restriction Fragment Length Polymorphism Assay to Detect and Differentiate between Infections with PCV-1 and PCV-2". Journal of Clinical Microbiology, vol. 38, No. 7, Jul. 2000, pp. 2494-2503.
Opriessnig et al., "A commercial vaccine based on PCV2a and an experimental vaccine based on a variant mPCV2b are both effective in protecting pigs against challenge with a 2013 U.S. variant mPCV2b strain". Vaccine, vol. 32, No. 2, 2014, pp. 230-237.
Fort et al., "Porcine circovirus type 2 (PCV2) vaccination of conventional pigs prevents viremia against PCV2 isolates of different genotypes and geographic origins". Vaccine, vol. 26, No. 8, 2008, pp. 1063-1071.
Opriessnig et al., "Differences in virulence among porcine circovirus type 2 isolates are unrelated to cluster type 2a or 2b and prior infection provides heterologous protection". Journal of General Virology, vol. 89, No. 10, 2008, pp. 2482-2491.
Lin et al., "*Mycoplasma hyorhinis* in Taiwan: Diagnosis and isolation of swine pneumonia pathogen". Veterinary Microbiology, vol. 115, 2006, pp. 111-116.
Harms et al., "Three cases of porcine respiratory disease complex associated with porcine circovirus type 2 infection". Journal of Swine Health and Production, vol. 10, No. 1, 2002, pp. 27-30.
Brogden, Kim A., "Polymicrobial Diseases of Animals and Humans". Polymicrobial Diseases, Chapter 1, 2002, 19 pages. [Accessed at http://www.ncbi.nlm.nih.gov/books/NBK2477/?report=printable on Jul. 8, 2014].
Opriessnig et al., "Effect of Vaccination with Selective Bacterins on Conventional Pigs Infected with Type 2 Porcine Circovirus". Veterinary Pathology, vol. 40, 2003, pp. 521-529.
Poljak et al., "Spread of porcine circovirus associated disease (PCVAD) in Ontario (Canada) swine herds: Part I. Exploratory spatial analysis". BMC Veterinary Research, vol. 6, No. 59, 2010, pp. 1-15.
Smith et al., "Observations on Experimental Oral Infection with *Salmonella dublin* in Calves and *Salmonella choleraesuis* in Pigs". Journal of Pathology and Bacteriology, vol. 93, No. 1, 1967, pp. 141-156.
Poppe et al., "*Salmonella typhimurium* DT104: A virulent and drug-resistant pathogen". Canadian Veterinary Journal, vol. 39, 1998, pp. 559-565.
Segalés et al., "Postweaning Multisystemic Wasting Syndrome and Porcine Circovirus Ty;e 2: The European Perspective". Trends in Emerging Viral Infections of Swine, Ch. 9.3, PMWS and PCV2: European Perspective, 2002, pp. 297-303.
Fablet et al., "A Case Study of Neonatal Diarrhoea in a Farrow-to-Finish Pig Farm". International Society for Animal Hygiene, Saint Malo, 2004, p. 151.
Dugdale et al., "Immune Response". Medline Plus Medicial Encyclopedia, Updated May 30, 2012, pp. 1-4. [Accessed at http://www.nlm.nih.gov/medlineplus/cncy/article/000821.htm on Mar. 19, 2014].
Patterson et al., "Baculovirus and Insect Cell Gene Expression: Review of Baculovirus Biotechnology". Environmental Health Perspectives, vol. 103, Nos. 7-8, Jul.-Aug. 1995, pp. 756-759.
Patterson et al., "Interlaboratory Comparison of Porcine Circovirus-2 Indirect Immunofluorescent Antibody Test and Enzyme-Linked Immunosorbent Assay Results on Experimentally Infected Pigs". Journal of Veterinary Diagnostic Investigation, vol. 23, 2011, pp. 206-212.
Ragona et al., "The Transcriptional Factor Egr-1 Is Synthesized by Baculovirus-Infected Insect Cells in an Active, DNA-Binding Form". DNA and Cell Biology, vol. 10, No. 1, 1991, pp. 61-66.
Rodríguez-Arrioja et al., "Dynamics of procine circovirus type 2 infection in a herd of pigs with postweaning multisystemic wasting syndrome". American Journal of Veterinary Research, vol. 63, No. 3, Mar. 2002, pp. 354-357.
Roesler et al., "Oral vaccination of pigs with an invasive gyrA-cpxA-rpoB *Salmonella typhimurium* mutant". Vaccine, vol. 23, No. 5, Dec. 2004, pp. 595-603.
Rotto, Hans "Diagnosis, Vaccination and Field Experiences with PCV-AD". Iowa Pork Progress, 2007, pp. 1-10.
Schaefer et al., "Characterization and Formulation of Multiple Epitope-Specific Neutralizing Monoclonal Antibodies for Passive Immunization against Cryptosporidiosis". Infection and Immunity, vol. 68, No. 5, May 2000, pp. 2608-2616.
Sedlik et al., "Recombinanat parvovirus-like particles as an antigen carrier: A novel nonreplicative exogenous antigen to elicit protective antiviral cytotoxic T cells". Proceedings of the National Academy of Sciences, vol. 94, Jul. 1997, pp. 7503-7508.
Segales et al., "Pathological findings associated with naturally acquired porcine circovirus type 2 associated disease". Veterinary Microbiology, vol. 98, 2004, pp. 137-149.
Segalés et al., "Immunosuppression in postweaning multisystemic wasting syndrome affected pigs". Veterinary Microbiology, vol. 98, 2004, pp. 151-158.
Segalés et al., "Porcine Circovirus Diseases". Diseases of Swine, 9th Edition, Chapter 14, Blackwell Publishing, Ames, Iowa, 2006, pp. 299-307.
Spier, R.E., "Multivalent Vaccines: Prospects and Challenges". Folia Microbiologica, vol. 42, No. 2, 1997, pp. 105-112.
Suradhat et al., "The influence of maternal immunity on the efficacy of a classical swine fever vaccine against classical swine fever virus, genogroup 2.2, infection". Veterinary Microbiology, vol. 92, 2003, pp. 187-194.
Thacker et al., "Effect of vaccination on the potentiation of porcine reproductive and respiratory syndrom virus (PRRSV)-induced pneumonia by *Mycoplama hyopneumoniae*". Vaccine, vol. 18, 2000, pp. 1244-1252.
Thacker, Eileen L., "Diagnosis of *Mycoplama hyopneumoniae*". Journal of Swine Health Production, vol. 12, No. 5, 2004, pp. 252-254.
Truong et al., "Identification of an immunorelevant ORF2 epitope from porcine circovirus type 2 as a serological marker for experimental and natural infection". Archives of Virology, vol. 146, 2001, pp. 1197-1211.
UniProt Database Accession No. O91862 submitted Nov. 1, 1998 by Meehan et al., Characterization of novel circovirus DNAs associated iwth wasting sydromes in pigs. Journal of General Virology, 1998; 79: 2171-2179, 1 page.
UniProt Database Accession No. Q9YTB6, Direct Submission, Wang et al., May 1, 1999, 1 page.
Wan et al., "Comprehensive Prevention and Control Techniques for Porcine Circovirus Type 2 Infection". Chinese Swine Industry, No. 3, 2006, pp. 42-45.
Wang et al., "Construction and immunogenicity of recombinant adenovirus expressing the capsid protein of porcine circovirus 2 (PCV2) in mice". Vaccine, vol. 24, 2006, pp. 3374-3380.
Weibel, Helen, "A field efficacy study with Enterisol® Ileitis and Ingelvac CircoFLEX® in Switzerland". Universität Zürich, 2009, 1 page. [Accessed at: http://www.vet.uzh.ch/dissertationen/diss_anzeige.php?ID=724&sprache=e on Jun. 7, 2013].
Williams et al., "Combined vaccines and simultaneous administration: Current issues and perspectives". Annals of the New York Academy of Sciences, vol. 754, 1995, pp. xi-xv, 35-47.
Wu et al., "Replication, Integration, and Packaging of Plasmid DNA following Cotransfection with Baculovirus Viral DNA". Journal of Virology, vol. 73, No. 7, Jul. 1999, pp. 5473-5480.

(56) References Cited

OTHER PUBLICATIONS

Xia et al., "Preparation of and Immunity Tests with Canine Coronavirus BEI Inactivated Vaccine". Chinese Journal of Veterinary Medicine, vol. 37, No. 3, 2001, pp. 37-38.
Yamada et al., "Evaluation of the Efficacy of Inactivated Vaccine against Salmonella Enteritidis Infection in Chicken". Journal of the Japanese Society on Poultry Diseases, vol. 35, No. 1, 1999, pp. 13-21. (English Summary at p. 21).
Yuan et al., "Immunology of the porcine respiratory disease complex". Animal Science Abroad in Pigs and Poultry, No. 5, 2002, pp. 36-38.
Opriessnig et al., "A PCV2 vaccine based on genotype 2b is more effective than a 2a-based vaccine to protect against PCV2b or combined PCV2a/2b viremia in pigs with concurrent PCV2, PRRSV and PPV infection". Vaccine, vol. 31, 2013, pp. 487-494.
Beach et al., "Efficacy and future prospects of commercially available and experimental vaccines against porcine circovirus type 2 (PCV2)". Virus Research, vol. 164, 2012, pp. 33-42.
Shen et al., "Comparison of commercial and experimental porcine circovirus type 2 (PCV2) vaccines using a triple challenge with PCV2, porcine reproductive and respiratory syndrome virus (PRRSV), and porcine parvovirus (PPV)". Vaccine, vol. 28, 2010, pp. 5960-5966.
Martelli et al., "One dose of a porcine circovirus 2 subunit vaccine induces humoral and cell-mediated immunity and protects against porcine circovirus-associated disease under field conditions". Veterinary Microbiology, vol. 149, 2011, pp. 339-351.
"Calendar, Mar. 2007". 3rd Annual Pig Veterinary Society Congress, vol. 37, No. 2, 2007, p. 33. [Accessed at http://www.piginternational-digital.com/piginternational/2007013//Print . . . on Aug. 3, 2012].
"General Methods 6xHis and GST Purification Direct Cloning". Baculovirus Expression Vector System Manual, 6th Edition, May 1999, pp. 1-108.
"H-V11-Postweaning multisystemic wasting syndrome-Lymph node-Pig". Read-Only Case Details Reviews: Mar. 2009, pp. 1-4. [Accessed at http://www.askjpc.org/vspo/show_page.php?id=800 on Dec. 14, 2013].
Allan et al., "PCV2; ticking time bomb?" Pig Progress, vol. 18, No. 5, 2002, pp. 14-12.
Bahnemann, Hans G., "Inactivation of Viruses in Serum with Binary Ethyleneimine". Journal of Clinical Microbiology, vol. 3, No. 2, Feb. 1976, pp. 209-210.
Banholzer, E. "A Follow-Up: PCV2, PRRS, *Mycoplasma hyopneumoniae*, Improvac". IPVS Congress, Jul. 16-19, 2006, pp. 1-20.
Begue et al., "Future Combined Vaccines". Journal of Infectious Diseases, vol. 173, Supp 3, 1996, pp. S295-S297.
Beseme et al., "Vaccination strategies for the control of circoviral diseases in pigs: PMWS and PCV2-associated PRDC". Proceedings of the Japanese Pig Veterinary Society, vol. 49, 2006, pp. 15-38.
Blanchard et al., "An ORF2 protein-based ELISA for porcine circovirus type 2 antibodies in post-weaning multisystemic wasting syndrome". Veterinary Microbiology, vol. 94, 2003, pp. 183-194.
Chung et al., "Real-time PCR for quantitation of porcine reproductive and respiratory syndrome virus and porcine circovirus type 2 in naturally-infected and challenged pigs". Journal of Virological Methods, vol. 124, 2005, pp. 11-19.
Ellis, John A., "Porcine circovirus: An old virus in a new guise causes an emerging disease thorugh a novel pathogenesis". Large Animal Veterinary Rounds, vol. 3, No. 4, Apr. 2003, pp. 1-6.
Fan et al., "Preclinical study of influenza virus A M2 peptide conjugate vaccines in mice, ferrets, and rhesus monkeys". Vaccine, vol. 22, 2004, pp. 2993-3003.
Fan et al., "The Expression of Porcine Circovirus Type 2 ORF2 Gene in Insect Cells and its Character". Chinese Journal of Biotechnology, vol. 21, No. 6, Nov. 2005, pp. 975-978.
GenBank Accession No. AF201311, Direct Submission, submitted Feb. 23, 2000 in Mankertz et al., "Characterization of PCV-2 isolates from Spain, Germany and France", Virus Research, vol. 66, No. 1, 2000, pp. 65-77, 2 pages.
Gizurarson, Sveinbjörn, "Clinically Relevant Vaccine-Vaccine Interactions". BioDrugs, vol. 9, No. 6, Jun. 1998, pp. 443-453.
Gualandi et al., "The Ability by Different Preparations of Porcine Parvovirus to Enhance Humoral Immunity in Swine and Guinea Pigs". Microbiologica, vol. 11, No. 4, 1988, pp. 363-369.
Gualandi et al., "The Response of Pregnant Gilts Previously Given an Inactivated Preparation of Porcine Parvovirus (PPV) to Challenge Infection with a Fully Virulent PPV". Microbiologica, vol. 15, 1992, pp. 391-396.
Haiwick et al., "Trivalent vaccine mixture protects against simultaneous challenge with *M. hyopneumoniae*, PCV2, and PRRS virus". Allen D. Leman Swine Conference, 2010, p. 176.
Hamel et al., "Nucleotide Sequence of Porcine Circovirus Associated with Postweaning Multisystemic Wasting Syndrome in Pigs". Journal of Virology, vol. 72, No. 6, Jun. 1998, pp. 5262-5267.
Harding et al., "Recognizing and diagnosing postweaning multisystemic wasting syndrome (PMWS)". Swine Health and Production, vol. 5, No. 5, 1997, pp. 201-203.
Haruna et al., "The role of immunostimulation in the development of postweaning multisystemic wasting syndrome in pigs under field conditions". Canadian Journal of Veterinary Research, vol. 70, Oct. 2006, pp. 269-276.
Hilgers et al., "Alkyl-esters of polyacrylic acid as vaccine adjuvants". Vaccine, vol. 16, No. 16, 1998, pp. 1575-1581.
Hirai et al., "Dual infection with PCV-2 and porcine epidemic diarrhoea virus in neonatal piglets". The Veterinary Record, vol. 148, 2001, pp. 482-484.
Hoogland et al., "Effects of adjuvants on porcine circovirus type 2-associated lesions". Journal of Swine Health and Production, vol. 14, No. 3, 2006, pp. 133-139.
Huang et al., "Porcine circovirus type 2 (PCV2) infection decreases the efficacy of an attenuated classical swine fever virus (CSFV) vaccine". Veterinary Research, vol. 42, 115, 2011, pp. 1-9.
Hüser et al., "Baculovirus Vectors: Novel Mammalian Cell Gene-Delivery Vehicles and Their Applications". American Journal of Pharmacogenomics, vol. 3, No. 1, 2003, pp. 53-63.
Invitrogen Life Technologies, "Growth and Maintenance of Insect Cell Lines". Insect Cell Lines Manual, Version K, Jul. 12, 2002, pp. 1-34. [Accessed at http://www.med.unc.edu/pharm/sondeklab/Lab%20Resources/manuals/insect_cell_manual.pdf on Nov. 25, 2013].
Iowa State University, "Lyphoid Depletion: PCV2-Associated Lymphoid Depletion"., 2013, pp. 1-2. [Accessed at: http://vetmed.iastate.edu/research/labs/pcv2/pcv2-associated-disease/lymphoid-depleti . . . on Dec. 14, 2013].
Jiang et al., "Expression, Self-Assembly, and Antigenicity of the Norwalk Virus Capsid Protein". Journal of Virology, vol. 66, No. 11, Nov. 1992, pp. 6527-6532.
Jiang et al., "Synthesis of rotavirus-Like Particles in Insect Cells: Comparative and Quantitative Analysis". Biotechnology and Bioengineering, vol. 60, No. 3, 1998, pp. 369-374.
Kennedy et al., "Repdocution of Lesions of Postweaning Multisystemic Wasting Syndrome by Infection of Conventional Pigs with Porcine Circovirus Type 2 Alone or in a Combination with Porcine Parvovirus". Journal of Comparative Pathology, vol. 122, 2000, pp. 9-24.
Kiupel, M. "Postweaning Multisystemic Wasting Syndrome (PMWS) in pigs". Production diseases in Farm Animals, 12th International Conference, Section D, Wageningen Academic Publishers, The Netherlands, 2006, pp. 74-89.
Kovacs et al., "The live attenuated bovine viral diarrhea virus components of a multi-valent vaccine confer protection against fetal infection". Veterinary Microbiology, vol. 96, 2003, pp. 117-131.
Kyriazakis et al., "The Maintenance of Health". Whittemore's Science and Practice of Pig Production, Third Edition, Chapter 7, Blackwell Publishing Ltd., Oxford, UK, 2006, pp. 263-316.
Lekcharoensuk et al., "Epitope Mapping of the Major Capsid Protein of Type 2 Porcine Circovirus (PCV2) by Using Chimeric PCV1 and PCV2". Journal of Virology, vol. 78, No. 15, Aug. 2004, pp. 8135-8145.
Li et al., "Expression and Self-Assembly of Empty Virus-Like Particle of Hepatitis E Virus". Journal of Virology, vol. 71, No. 10, Oct. 1997, pp. 7207-7213.

(56) References Cited

OTHER PUBLICATIONS

Liu et al., "Development of an ELISA Baed on the Baculovirus-Expressed Capsid Protein of Porcine Circovirus Type 2 as Antigen". Journal of Veterinary Medical Science, vol. 66, No. 3, Mar. 2004, pp. 237-242.

McKeown et al., "Effects of Porcine Circovirus Type 2 (PCV2) Maternal Antibodies on Experimental Infection of Piglets with PCV2". Clinical and Diagnostic Laboratory Immunology, vol. 12, No. 11, Nov. 2005, pp. 1347-1351.

Meehan et al., "Characterization of novel circovirus DNAs associated with wasting syndromes in pigs". Journal of General Virology, vol. 79, 1998, pp. 2171-2179.

Mortola et al., "Efficient assembly and release of SARS coronavirus-like particles by a heterologous expression system". FEBS Letters, vol. 576, 2004, pp. 174-178.

Muirhead, Mike, "Sources of information on PMWS/PDNS". The Veterinary Record, vol. 150, No. 14, Apr. 6, 2002, p. 456.

Murakami et al., "Occurrence of Swine Salmonellosis in Postweaning Multisystemic Wasting Syndrome (PMWS) Affected Pigs Concurrently Infected with Porcine Reproduction and Respiratory Syndrome Virus (PRRSV)". Journal of Veterinary Medical Science, vol. 68, 2006, pp. 387-391.

Neutra et al., "Optimization of protein-production by the baculovirus expression vector system in shake flasks". Applied Microbiology and Biotechnology Journal, vol. 37, No. 1, 1992, pp. 74-78.

Noad et al., "Virus-like particles as immunogens" Trends in Microbiology, vol. 11, No. 9, Sep. 2003, pp. 438-444.

O'Dea et al., "Porcine circovirus-associated disease in weaner pigs in Western Australia". Australian Veterinary Journal, vol. 89, No. 4, Apr. 2011, pp. 122-130.

Ohnesorge et al., "Efficacy Studies—Efficacy evaluation of a mixed *Mycoplasma hyopneumoniae* bacterin and a porcine circovirus type 2 vaccine". 2007, 1 page. [Accessed at http://www.ingelvacflex.co.uk/mycoflex/research/efficacy.php on Jul. 31, 2012].

Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, 2002, pp. 11837-11844.

Opriessnig et al., "Effects of the timing of the administration of *Mycoplasma hyopneumoniae* bacterin on the development of lesions associated with porcine circovirus type 2". Veterinary Record, vol. 158, No. 5, Feb. 2006, pp. 149-154.

Opriessnig et al., "Experimental Co-Infection with Porcine Circovirus Type 2 and *Salmonella typhimurium* or *Lawsonia intracellularis*". Pig Progress, Jun. 2008, 1 page. [Accessed at: http://www.pigprogress.net/public/file/IPVS-oral%20presentations/Viral%20diseases/Experimental%20co-infection%20with%20PCV2%20and%20salmonella%20Typhimurium%20or%20lawsonia%20intracellularis.pdf on Mar. 17, 2010].

Paterson, J.E., "Health and antimicrobial resistance". Manipulating Pig Production X, Chapter 2, Proceedings of the Tenth Biennial Conference of the Australasian Pig Science Association (Inc.) (APSA) held in Christchurch, New Zealand on Nov. 27 to 30, 2005, Werribee, Victoria, Australia: Australasian Pig Association (Inc.), pp. 21-74.

EMBL Acession No. ACA49867, Wang et al., "Porcine circovirus-2 capside protein"., Mar. 5, 2008, 1 page.

EMBL Acession No. ACA49861, Wang et al., "Porcine circovirus-2 capside protein"., Mar. 5, 2008, 1 page.

EMBL Acession No. ACV53224, Cortey et al., "Porcine circovirus-2 partial capsid protein"., Sep. 13, 2009, 1 page.

""PRRS Plus"—PRRS Virus Infection in Combination with OTher Agents PG Halbur". 2003 PRRS Compendium Producer Edition, 2003, pp. 18-24. [Accessed at http://old.pork.org/filelibraiy/prrs/2003compendium/prrschapter3.pdf on Jun. 2, 2015].

Opriessnig et al., "Effect of porcine parvovirus vaccination on the development of PMWS in segregated early weaned pigs coinfected with type 2 porcine circovirus and porcine parvovirus". Veterinary Microbiology, vol. 98, 2004, pp. 209-220.

\* cited by examiner

REDUCTION OF CONCOMITANT INFECTIONS IN PIGS BY THE USE OF PCV2 ANTIGEN

RELATED APPLICATIONS

This application is a continuation of U.S. patent application Ser. No. 12/941,836, filed Nov. 8, 2010, now patented as U.S. Pat. No. 8,475,805, which is a continuation of U.S. patent application Ser. No. 12/198,721 filed Aug. 26, 2008, now patented as U.S. Pat. No. 7,829,274, the teachings and content of which are hereby incorporated by reference.

SEQUENCE LISTING

This application contains a sequence listing in paper format and in computer readable format, the teachings and content of which are hereby incorporated by reference. The sequence listing is identical with that incorporated in WO06/072065.

BACKGROUND OF THE INVENTION

1. Field of the Invention

The present invention relates to the field of veterinary medicine, in particular to infectious diseases. Moreover, the present invention relates to a method for reducing concomitant infections in pigs caused by pathogens other than PCV-2.

2. Background

In 1996 a new emerging disease termed "Postweaning Multisystemic Wasting Syndrome" (PMWS) was described in reference to cases observed in Canada five years earlier (Clark T. Pathology of the Postweaning Multisystemic Wasting Syndrome of Pigs. 1996 p. 22-5). Porcine cirocvirus type 2 (PCV2) was identified as an essential causative agent of this disease syndrome. PMWS has meanwhile been observed in virtually all regions of the world that produce pigs (Brunborg I M, Moldal T, Jonassen C M. J Virol Methods 2004 Dec. 15; 122(2):171-8). Pigs 5 to 15 weeks of age are most commonly affected (Allan G, McNeilly F. PMWS/PCVD: Diagnosis, Disease and Control: What do we know? 2006 Jul. 16-2006 Jul. 19; 2006; Allan G M, et al., Vet Microbiol 2004 Feb. 4; 98(2):165-8; Chae C. Vet J 2004 July; 168(1):41-9). Clinical signs include a marked increase in the mortality rate, wasting, generalized enlargement of lymphnodes, respiratory signs, and occasionally pallor, jaundice and diarrhoea (Chae C. Vet J 2005 May; 169(3):326-36; Segales J. et al. Vet Microbiol 2004 Feb. 4; 98(2):151-8). These clinical signs are not all seen at the same time in a single PMWS affected pig herd but it appears that the expression of clinical signs is indirectly linked to farm-specific co-pathogens that preferentially target different organ systems (Krakowka S. et al., Vet Pathol 2001 January; 38(1):31-42). Epidemiological investigations have shown that porcine reproductive and respiratory syndrome virus (PRRSV), swine influenza virus (SIV), porcine parvovirus (PPV), *Haemophilus parasuis*, *Actinobacillus pleuropneumoniae* (APP), *Streptococcus suis* and *Mycoplasma hyopneumoniae* (Chae C. Vet J 2004 July; 168(1):41-9) are most commonly seen in combination with the disease syndrome.

For the production of PMWS activation of the immune system has been postulated to be the pivotal event (Krakowka S. et al., Vet Pathol 2001 January; 38(1):31-42). While the experimental inoculation with PCV2 alone did only produce clinically asymptomatic infections and a very modest histologic evidence of inflammation the dual infection with PCV2 and PPV or PRRSV resulted in more severe clinical signs, gross and histological lesions, a wider spread and a higher PCV2 viral load within affected tissues. These findings seem to be predominantly caused by PCV2 since infection with PRRSV or PPV alone did not result in comparable clinical signs or lesions (Allan et al., J Comp Pathol 1999 July; 121 (1):1-11; Allan G M, et al., Arch Virol 2000; 145(11):2421-9; Harms P A, et al., Vet Pathol 2001 September; 38(5):528-39; Krakowka S, et al., Vet Pathol 2000 May; 37(3):254-63; Ostanello F, et al., Vet Microbiol 2005 Jul. 1; 108(3-4):179-86; Rovira A, et al., J Virol 2002 April; 76(7):3232-9). In addition, a similar increase in disease severity could also be achieved in the absence of other co-infecting agents if pigs were immunostimulated with keyhole limpet hemocyanin in incomplete Freund's adjuvant (KLH/ICFA) (Krakowka S. et al., Vet Pathol 2001 January; 38(1):31-42).

The effects of PCV2 on the pig immune system are not fully known. It has been reported that the main target cells for PCV2 replication are the monocyte/macrophage lineage as well as other antigen presenting cells such as follicular dendritic cells (Darwich L, et al., Arch Virol 2004 May; 149(5): 857-74). Several studies suggested that PCV2 infects dividing cells, macrophages and B lymphocytes, inducing apoptosis of the B cells that leads to the damage of lymphoid tissues resulting in extensive lymphocyte depletion (Darwich L, et al., Arch Virol 2004 May; 149(5):857-74). Particularly PMWS affected pigs show histiocytic infiltration and lymphocyte depletion of both follicle centers and parafollicular zones, symptoms associated with the presence of PCV2 (Segales J. et al. Vet Microbiol 2004 Feb. 4; 98(2):151-8; Darwich L, et al., Arch Virol 2004 May; 149(5):857-74). These facts have led some to suggest that PCV2 infection might cause immunosuppression (Darwich L, et al., Arch Virol 2004 May; 149(5):857-74; Krakowka S, et al., Viral Immunol 2002; 15(4):567-82).

Approaches to treat PCV2 infections, in particular PMWS, based on a DNA vaccine are described in U.S. Pat. No. 6,703,023. In WO 03/049703 production of a live chimeric vaccine is described, comprising a PCV1 backbone in which an immunogenic gene of a pathogenic PCV2 strains replaces a gene of the PCV1 backbone. WO99/18214 has provided several PCV2 strains and procedures for the preparation of a killed PCV2 vaccine. An effective ORF-2 based subunit vaccine has been reported in WO06/072065. Any of such vaccines are intended to be used for the vaccination/treatment of swine against PMWS.

No reports exist about the potential impact of PCV2 infections on the incidence of concomitant infections caused by various swine relevant pathogens. Particularly, nothing is reported about the potential impact of PCV2 on specific pathogens, such as *Actinobacillus pleuropneumoniae*, *Haemophilus parasuis*, *Mycoplasma hyorhinis*, *Pasteurella multocida*, PRRSV, *Salmonella* spp., SIV or *Streptococcus suis*. Moreover, even if different PCV2 vaccines are known for a short time, their impact on concomitant infections other than PCV2 in swine is yet not known.

DESCRIPTION OF THE INVENTION

Figure 1A:
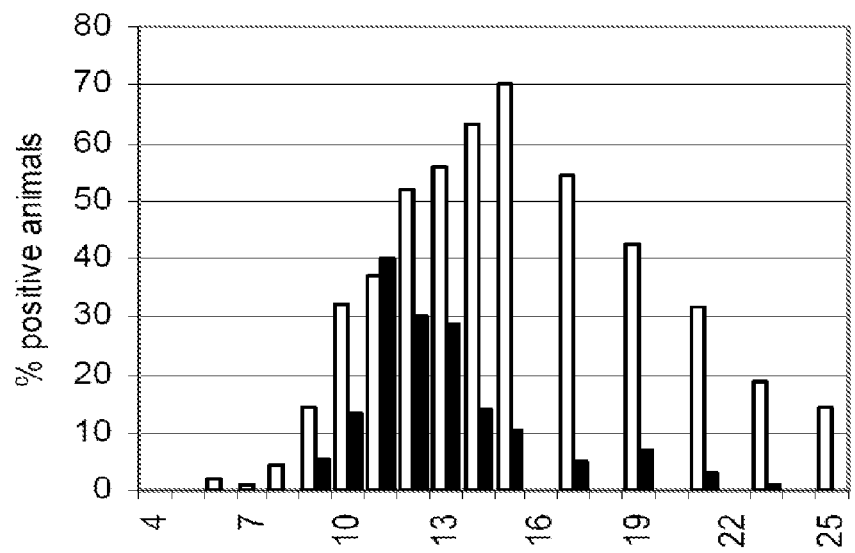
FIG. 1A is a profile of PCV2 viraemia. Blood samples from 110 pre-selected placebo-treated animals were collected at the indicated time points. On the basis of the quantitative PCR results animals were grouped into classes of animals with sub-clinical viral loads ($10^4$-$10^6$ gE/ml) and clinical relevant viral loads ($>10^6$ gE/ml). White bars represent the proportion of animals with subclinical viral loads and black bars illustrate the proportion of animals with clinical relevant viral loads per sampling day.

The present invention is based on the surprising finding, that PCV2 vaccine cannot only reduce the percentage of PCV2 infections in pigs or a herd of pigs, but also the percentage of concomitant infections caused by pathogens other than circovirus, in particular other than PCV2.

Therefore, according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen.

The term "concomitant infections" as used herein shall mean but is not limited to any infection of swine caused by viral, bacterial, fungal or worm pathogens other than circovirus, in particular other than PCV2. The term "concomitant pathogen" as used herein means but is not limited to a pathogen of swine other than circovirus, in particular other than PCV2. Thus according to another aspect, the present invention provides a method for reducing the percentage of concomitant infections in pigs or a herd of pigs caused by one or more viral, bacterial, fungal or worm pathogens other than circovirus, in particular other than PCV2 comprising the step administering to said pig(s) an effective amount of PCV2 antigen or an immunogenic composition comprising PCV2 antigen. Preferably, the concomitant infections are caused by one or more bacterial, viral or fungal pathogens, or combinations thereof. More preferred, the concomitant infections are caused by one or more bacterial or viral pathogens, or a combination thereof.

According to another aspect of the present invention, the term "concomitant infections" also means that the pig infected with one or more concomitant pathogens other than circovirus, in particular other than PCV2 is co-infected with PCV2. Thus according to another aspect, the present invention provides a method for reducing the percentage of concomitant infections in pigs or a herd of pigs co-infected with PCV2, wherein the concomitant infections are caused by one or more pathogens other than circovirus, in particular other than PCV2 comprising the step administering to said pig(s) an effective amount of PCV2 antigen or an immunogenic composition comprising PCV2 antigen. Preferably, the concomitant infections are caused by one or more viral, bacterial, fungal or worm pathogens other than circovirus, in particular other than PCV2.

The term "co-infected with PCV2" as used herein means but is not limited to any form of co-infection with PCV2, which means that the PCV2 infection occurs prior to, simultaneously with or after the infection with the pathogens which are different from circovirus, in particular different from PCV2. It also includes sub-clinical, clinical apparent, fulminant and chronic courses of PCV2 infections. In this context, apparent courses are not limited to PMWS, but also include any other clinical appearances of PCV2 infections such as porcine respiratory disease complex (PRDC), porcine dermatopathy and nephropathy syndrome (PDNS), reproductive failure, granulomatous enteritis, potentially, congenital tremors (CT-AII) and perinatal myocarditis (Chae, Veterinary J., 2005; 169: 326-336).

However, the term "concomitant infection" does not necessarily mean that the pig or herd of pigs is co-infected with PCV2. The term "concomitant infection" also refers but is no limited to cases, where pigs or a herd of pigs are/is exposed to PCV2 or where a risk exist to get infected with PCV2. Thus according to another aspect, the present invention provides a method for reducing the percentage of concomitant infections in pigs or a herd of pigs exposed to PCV2, or endangered or susceptible to get infected with PCV2, wherein the concomitant infections are caused by one or more pathogens other than circovirus, in particular other than PCV2 comprising the step administering to said pig(s) an effective amount of PCV2 antigen or an immunogenic composition comprising PCV2. Preferably, the concomitant infections are caused by one or more viral, bacterial, fungal or worm pathogens other than circovirus, in particular other than PCV2.

The term "the percentage of concomitant infections is reduced" shall mean that the number of pigs infected with a pathogen other than circovirus, is reduced for said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. In this context the term "non-vaccinated control group" shall mean a group of pigs which are not administered with an effective amount of PCV2 antigen or an immunogenic composition comprising PCV2 antigen. Thus, according to another aspect, the present invention also provides a method for reducing the percentage of concomitant infections in pigs or a herd of pigs caused by a pathogen other than PCV2 comprising the step administering to said pig(s) an effective amount of PCV2 antigen or an immunogenic composition comprising PCV2 antigen, wherein the number of pigs infected with said pathogen other than circovirus, is reduced for said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. Preferably, the concomitant infection is caused a by viral, bacterial or fungal pathogen other than circovirus, in particular other than PCV2. More preferably, said pigs or herd of pigs are co-infected with PCV2 as defined above, exposed to PCV2, or endangered or susceptible to get infected with PCV2.

Concomitant infections caused by a viral, bacterial or fungal pathogen other than circovirus, in particular other than PCV2 may cause enteric, respiratory, reproductive, central nervous or locomotory symptoms in the infected animals. Incidence of any of those clinical symptoms, caused the by the respective pathogens can be reduced. Thus according to another aspect, the present invention relates to a method for reducing the percentage of concomitant infections in pigs or a herd of pigs caused by one or more enteric, respiratory, reproductive, central nervous or locomotory pathogens other than PCV2 comprising the step administering to said pig(s) an effective amount of PCV2 antigen or an immunogenic composition comprising PCV2 antigen. Preferably, said pigs are co-infected with PCV2 as defined above, exposed to PCV2, or endangered or susceptible to get infected with PCV2. More preferred, the number of pigs infected with an enteric, respiratory, reproductive, central nervous or locomotory pathogen other than circovirus, is reduced for said enteric, respiratory, reproductive, central nervous or locomotory pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

Enteric pathogens are for example *Lawsonia intracellularis, E. coli, Streptococcus suis, Clostridium* spp, *Salmonella* spp., *Brachyspira* spp., rotaviruses or coronaviruses. Respiratory pathogens are for example PRRSV, *Mycoplasma hyopneumoniae, M. hyorhinis*. Reproductive pathogens are for example *Leptospira* spp., PRRSV, *Chlamydia* spp. Locomotory pathogens are for example *S. suis, M. hyorhinis, Erysipelotrix rusiopathiae*. Pathogens of the central nervous system are for example Pseudorabies virus, *S. suis., Haemophilus* sp.

In general the term "pathogen other than PCV2" means but is not limited to one or more of the pathogens selected from the group consisting of: *Actinobacillus suis; Arcanobacterium pyogenes; Actinobacillus pleuropneumonia* (APP); African swine fever virus; *Aspergillus* spp.; Astroviruses; *Ascaris suum; Blastocystis* spp.; *Bordetella bronchiseptica; Brachyspira* spp., *B. hyodysenteriae, B. pilosicoli; Brucella suis, Brucella suis* biovars 1, 2 and 3; *Candida* spp.; Classical swine fever virus; *Clostridium* spp., in particular *C. difficile, C. perfringens* types A, B and C, *C. novyi, C. septicum, C. difficile, C. tetani; Chlamydia* spp., *Cryptosporidium* spp.; Encephalomyocarditis virus; *Eperythrozoonosis suis; Erysipelothrix ruhsiopathiae; Escherichia coli; Fusarium* spp.; *Haemophilus parasuis*; Hemagglutinating encephalomyelitis virus; Hepatitis E virus; Japanese encephalitis virus; *Hyostrongylus rubidus; Lawsonia intracellularis; Leptospira* spp., *L. australis, L. canicola, L. grippotyphosa, L. pomona, L. icterohaemorrhagicae, L. interrogans, L. tarassovi, L. hardjo, L. sejroe, L. bratislava; Mannheimia haemolytica*; Menangle virus; *Mycobacterium* spp., *M. avium, M. intracellulare, M. tuberculosis; Mycoplasma* spp., *M. hyopneumoniae, M. hyorhinis*; Nipah virus; *Oesophagostum* spp., *Oesophagostum dentatum, Oesophagostum quadrospinulatum; Pasteurella* spp., *P. multocida; Penicillium* spp.; Porcine adenovirus; Porcine cytomegalovirus; Porcine enteric caliciviruses; Porcine enteric picornaviruses; Porcine parvovirus; Porcine respiratory corona virus; PRRS virus; Pseudorabies virus; Reovirus; Rotavirus; Rubulavirus; *Salmonella* spp., *S. typhimurium, S. choleraesuis, S. dublin; Sarcoptes* spp.; *Staphylococcus hyicus; Streptococcus* spp., *S. suis, S. porcinus, S. dysgalactiae, S. dysgalactiae* subsp. *equisimilis; Strongyloides ransomi*; Swine herpes virus; Swine influenza virus; Swine pox virus; Transmissible gastroenteritis virus; *Trichuris* spp. *Taenia* spp., *Trichinella spiralis*; Vesicular stomatitis virus; Virus of vesicular exanthema of swine; West Nile virus; or *Yersina* spp., *Y. pseudotuberculosis, Y. enterocolitica*.

Thus according to another aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein the pathogens cause the concomitant infections are selected from the group consisting of: *Actinobacillus suis; Arcanobacterium pyogenes; Actinobacillus pleuropneumonia* (APP); African swine fever virus; *Aspergillus* spp.; Astroviruses; *Ascaris suum; Blastocystis* spp.; *Bordetella bronchiseptica; Brachyspira* spp., *B. hyodysenteriae, B. pilosicoli; Brucella suis, Brucella suis* biovars 1, 2 and 3; *Candida* spp.; Classical swine fever virus; *Clostridium* spp., in particular *C. difficile, C. perfringens* types A, B and C, *C. novyi, C. septicum, C. difficile, C. tetani; Chlamydia* spp., *Cryptosporidium* spp.; Encephalomyocarditis virus; *Eperythrozoonosis suis; Erysipelothrix ruhsiopathiae; Escherichia coli; Fusarium* spp.; *Haemophilus parasuis*; Hemagglutinating encephalomyelitis virus; Hepatitis E virus; Japanese encephalitis virus; *Hyostrongylus rubidus; Lawsonia intracellularis; Leptospira* spp., *L. australis, L. canicola, L. grippotyphosa, L. pomona, L. icterohaemorrhagicae, L. interrogans, L. tarassovi, L. hardjo, L. sejroe, L. bratislava; Mannheimia haemolytica*; Menangle virus; *Mycobacterium* spp., *M. avium, M. intracellulare, M. tuberculosis; Mycoplasma* spp., *M. hyopneumoniae, M. hyorhinis*; Nipah virus; *Oesophagostum* spp., *Oesophagostum dentatum, Oesophagostum quadrospinulatum; Pasteurella* spp., *P. multocida; Penicillium* spp.; Porcine adenovirus; Porcine cytomegalovirus; Porcine enteric caliciviruses; Porcine enteric picornaviruses; Porcine parvovirus; Porcine respiratory corona virus; PRRS virus; Pseudorabies virus; Reovirus; Rotavirus; Rubulavirus; *Salmonella* spp., *S. typhimurium, S. choleraesuis, S. dublin; Sarcoptes* spp.; *Staphylococcus hyicus; Streptococcus* spp., *S. suis, S. porcinus, S. dysgalactiae, S. dysgalactiae* subsp. *equisimilis; Strongyloides ransomi*; Swine herpes virus; Swine influenza virus; Swine pox virus; Transmissible gastroenteritis virus; *Trichuris* spp. *Taenia* spp., *Trichinella spiralis*; Vesicular stomatitis virus; Virus of vesicular exanthema of swine; West Nile virus; or *Yersina* spp., *Y. pseudotuberculosis, Y. enterocolitica*.

Preferably said concomitant infections are caused by one or more of the pathogens selected from the group consisting of: *Actinobacillus pleuropneumoniae; Haemophilus parasuis; Mycoplasma hyrhinis; Pasteurella multocida*; PRRS; *Salmonella* spp. and *Strepococcus suis*. Most preferred said concomitant infections are caused by one or more of the pathogens selected from the group consisting of: *Actinobacillus pleuropneumoniae; Haemophilus parasuis; Mycoplasma hyrhinis; Pasteurella multocida*; PRRS; *Salmonella* spp., and *Strepococcus suis*. More preferred said concomitant infections are caused by one or more of the pathogens selected from the group consisting of: *Actinobacillus pleuropneumoniae; Mycoplasma hyrhinis*, and PRRS. Most preferred by *Mycoplasma hyrhinis* and/or PRRS.

Preferably, said pigs are co-infected with PCV2 as defined above, exposed to PCV2, or endangered or susceptible to get infected with PCV2. More preferred, the number of pigs infected with one or more of said pathogens above other than circovirus, is reduced for said pathogens for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. In case of multiple infections, the reduction rates as described above refer to each specific pathogen. For example, reduction of more than 10% concomitant infections in a multiple infected pig means that the infection rate with regard to a specific pathogen is reduced for more than 10%. It does not necessarily mean that the infection rate with regard to all pathogen is reduced for more than 10% as compared to a non-vaccinated control group, or with regard to a herd of pigs that less than 10% of the pigs of said herd are infected by all of said pathogens.

The terms "PCV2 antigen" as used herein refer to an amino acid sequence which elicits an immune response against PCV2 in a host. An antigen, as used herein, includes the full-length sequence of any PCV2 proteins, analogs thereof, or immunogenic fragments thereof.

The term "immunogenic fragment" refers to a fragment of a protein which includes one or more epitopes and thus elicits the immune response in a host. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; Gardner et al., (1998) 12th World AIDS Conference, Geneva, Switzerland, Jun. 28-Jul. 3, 1998.

An "immune response" means but is not limited to the development in a host of a cellular and/or antibody-mediated immune response to an antigen, a immunogenic composition or vaccine of interest. Usually, an "immune response" includes but is not limited to one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number or severity of, or lack of one or more of the symptoms associated with PCV2 infections, in delay of onset of viremia, in a reduced viral persistence, in a reduction of the overall viral load and/or a reduction of viral excretion.

The terms "immunogenic composition" or "vaccine" (both terms are used synonymously) as used herein refers to any pharmaceutical composition containing a PCV2 antigen, which composition can be used to prevent or treat a PCV2 infection-associated disease or condition in a subject. A preferred immunogenic composition can induce, stimulate or enhance the immune response against PCV2. The term thus encompasses both subunit immunogenic compositions, as described below, as well as compositions containing whole killed, or attenuated and/or inactivated PCV2.

Thus according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein the immunogenic composition comprising PCV2 antigen a is subunit immunogenic composition, a compositions containing whole killed, or attenuated and/or inactivated PCV2. Preferably, said pigs are co-infected with PCV2 as defined above, exposed to PCV2, or endangered or susceptible to get infected with PCV2. More preferred, the number of pigs infected with said pathogens other than circovirus, is reduced with regard to one or more of said pathogens for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

The term "subunit immunogenic composition" as used herein refers to a composition containing at least one immunogenic polypeptide or antigen, but not all antigens, derived from or homologous to an antigen from PCV2. Such a composition is substantially free of intact PCV2. Thus, a "subunit immunogenic composition" is prepared from at least partially purified or fractionated (preferably substantially purified) immunogenic polypeptides from PCV2, or recombinant analogs thereof. A subunit immunogenic composition can comprise the subunit antigen or antigens of interest substantially free of other antigens or polypeptides from PCV2, or in fractionated from. A preferred immunogenic subunit composition comprises the PCV2 ORF-2 protein as described below. Most preferred are immunogenic subunit compositions, which comprise any of the PCV2 antigens provided in WO06/072065, which are all incorporated herein by reference in their entirety.

According to further aspect, the immunogenic composition as used herein most preferably comprises the polypeptide, or a fragment thereof, expressed by ORF-2 of PCV2. PCV2 ORF-2 DNA and protein, used herein for the preparation of the compositions and within the processes provided herein is a highly conserved domain within PCV2 isolates and thereby, any PCV2 ORF-2 would be effective as the source of the PCV2 ORF-2 DNA and/or polypeptide as used herein. A preferred PCV2 ORF-2 protein is that of SEQ ID NO: 11 of WO06/072065. A further preferred PCV ORF-2 polypeptide is provided as SEQ ID NO: 5 of WO06/072065. However, it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4 of WO06/072065. Moreover, the antigenic characteristic of a modified antigen is still retained, when the modified antigen confers at least 70%, preferably 80%, more preferably 90% of the protective immunity as compared to the PCV2 ORF-2protein, encoded by the polynucleotide sequence of SEQ ID NO:3 or SEQ ID NO:4 as provided in WO06/072065.

Thus according to one aspect, the present invention relates to a method for reducing the percentage of concomitant infections in pigs or a herd of pigs caused by pathogens other than PCV2 comprising the step administering to said pig(s) an effective amount of PCV2 antigen or an immunogenic composition comprising PCV2 antigen, wherein the PCV2 antigen is an antigen PCV2 ORF-2 protein that has at least 70%, preferably, 80% even more preferably 90% of the protective immunity as compared to compared to the PCV2 ORF-2 protein, encoded by the polynucleotide sequence of SEQ ID NO:3 or SEQ ID NO:4 as provided in WO06/072065. Preferably said PCV2 ORF-2 have the sequence of SEQ ID NO: 11 or SEQ ID NO: 5 of WO06/072065. Preferably, said pigs are co-infected with PCV2 as defined above, exposed to PCV2, or endangered or susceptible to get infected with PCV2. More preferred, the number of pigs infected with said pathogens other than circovirus, is reduced for more than 40%, preferable for more than 50%, more preferred for more than 60%, even more preferred for more than 80% even more preferred for more than 100% as compared to a non-vaccinated control group.

In some forms, immunogenic portions of PCV2 ORF-2 protein are used as the antigenic component in the immunogenic composition, comprising PCV2 antigen. The term "immunogenic portion" as used herein refers to truncated and/or substituted forms, or fragments of PCV2 ORF-2 protein and/or polynucleotide, respectively. Preferably, such truncated and/or substituted forms, or fragments will comprise at least 6 contiguous amino acids from the full-length ORF-2 polypeptide. More preferably, the truncated or substituted forms, or fragments will have at least 10, more preferably at least 15, and still more preferably at least 19 contiguous amino acids from the full-length PCV ORF-2 polypeptide. Two preferred sequences in this respect are provided as SEQ ID NO: 9 and SEQ ID NO:10 of WO06/072065. It is further understood that such sequences may be a part of larger fragments or truncated forms.

As mentioned above, a further preferred PCV2 ORF-2 polypeptide is any one encoded by the nucleotide sequences of SEQ ID NO: 3 or SEQ ID NO: 4. However, it is understood by those of skill in the art that this sequence could vary by as much as 6-20% in sequence homology and still retain the antigenic characteristics that render it useful in immunogenic compositions. In some forms, a truncated or substituted form, or fragment of this PVC2 ORF-2 polypeptide is used as the antigenic component in the composition. Preferably, such truncated or substituted forms, or fragments will comprise at least 18 contiguous nucleotides from the full-length PCV2 ORF-2 nucleotide sequence, e.g. of SEQ ID NO: 3 or SEQ ID NO: 4. More preferably, the truncated or substituted forms, or fragments, will have at least 30, more preferably at least 45, and still more preferably at least 57 contiguous nucleotides of the full-length PCV2 ORF-2 nucleotide sequence, e.g. SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, N.J. (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferably at least 100, even more preferably at least 250, and even more preferably at least 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein said PCV2 ORF-2 protein is anyone of those, described above. Preferably, said PCV2 ORF-2 protein is
  i) a polypeptide comprising the sequence of SEQ ID NO: 5, SEQ ID NO: 6, SEQ ID NO: 9, SEQ ID NO: 10 or SEQ ID NO: 11 of WO06/07065;
  ii) any polypeptide that is at least 80% homologous to the polypeptide of i),
  iii) any immunogenic portion of the polypeptides of i) and/or ii)
  iv) the immunogenic portion of iii), comprising at least 10 contiguous amino acids included in the sequences of SEQ ID NO: 5, SEQ ID NO: 6, SEQ ID NO: 9, SEQ ID NO: 10 or SEQ ID NO: 11 of WO06/072065,
  v) a polypeptide that is encoded by a DNA comprising the sequence of SEQ ID NO: 3 or SEQ ID NO: 4 of WO06/072065.
  vi) any polypeptide that is encoded by a polynucleotide that is at least 80% homologous to the polynucleotide of v),
  vii) any immunogenic portion of the polypeptides encoded by the polynucleotide of v) and/or vi)
  viii) the immunogenic portion of vii), wherein polynucleotide coding for said immunogenic portion comprises at least 30 contiguous nucleotides included in the sequences of SEQ ID NO: 3, or SEQ ID NO: 4 of WO06/072065.

Preferably any of those immunogenic portions have the immunogenic characteristics of PCV2 ORF-2 protein that is encoded by the sequence of SEQ ID NO: 3 or SEQ ID NO: 4 of WO06/07065.

Preferably, said infected pigs are co-infected with PCV2 as defined above, exposed to PCV2, or endangered or susceptible to get infected with PCV2. More preferred, the number of pigs infected with said pathogens other than circovirus, is reduced with regard to one or more of said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

According to a further aspect, PCV2 ORF-2 protein is provided in the immunogenic composition at an antigen inclusion level effective for the treatment of animals subclinically infected with PCV2. Preferably, the PCV2 ORF-2 protein inclusion level is at least 0.2 μg antigen/ml of the final immunogenic composition (μg/ml), more preferably from about 0.2 to about 400 μg/ml, still more preferably from about 0.3 to about 200 μg/ml, even more preferably from about 0.35 to about 100 μg/ml, still more preferably from about 0.4 to about 50 μg/ml, still more preferably from about 0.45 to about 30 μg/ml, still more preferably from about 0.6 to about 15 μg/ml, even more preferably from about 0.75 to about 8 μg/ml, even more preferably from about 1.0 to about 6 μg/ml, still more preferably from about 1.3 to about 3.0 μg/ml, even more preferably from about 1.4 to about 2.5 μg/ml, even more preferably from about 1.5 to about 2.0 μg/ml, and most preferably about 1.6 μg/ml.

According to a further aspect, the PCV ORF-2 antigen inclusion level is at least 0.2 μg/PCV2 ORF-2 protein as described above per dose of the final antigenic composition (μg/dose), more preferably from about 0.2 to about 400 μg/dose, still more preferably from about 0.3 to about 200 μg/dose, even more preferably from about 0.35 to about 100 μg/dose, still more preferably from about 0.4 to about 50 μg/dose, still more preferably from about 0.45 to about 30 μg/dose, still more preferably from about 0.6 to about 15 μg/dose, even more preferably from about 0.75 to about 8 μg/dose, even more preferably from about 1.0 to about 6 μg/dose, still more preferably from about 1.3 to about 3.0 μg/dose, even more preferably from about 1.4 to about 2.5 μg/dose, even more preferably from about 1.5 to about 2.0 μg/dose, and most preferably about 1.6 μg/dose.

The PCV2 ORF-2 polypeptide used in the immunogenic composition in accordance with the present invention can be derived in any fashion including isolation and purification of PCV2 ORF2, standard protein synthesis, and recombinant methodology. Preferred methods for obtaining PCV2 ORF-2 polypeptide are provided in WO06/072065, the teachings and content of which are hereby incorporated by reference in its entirety. Briefly, susceptible cells are infected with a recombinant viral vector containing PCV2 ORF-2 DNA coding sequences, PCV2 ORF-2 polypeptide is expressed by the recombinant virus, and the expressed PCV2 ORF-2 polypeptide is recovered from the supernatant by filtration and inactivated by any conventional method, preferably using binary ethylenimine, which is then neutralized to stop the inactivation process.

The immunogenic composition as used herein also refers to a composition that comprises i) any of the PCV2 ORF-2 protein described above, preferably in concentrations described above, and ii) at least a portion of the viral vector expressing said PCV2 ORF-2 protein, preferably of a recombinant baculovirus. Moreover, the immunogenic composition can comprise i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture supernatant.

Thus according to one aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein the PCV2 antigen is recombinant PCV2 ORF-2, preferably a baculovirus expressed PCV2 ORF-2. Preferably those recombinant or baculovirus expressed PCV2 ORF-2 having the sequence as described above.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, preferably of a recombinant baculovirus, and iii) a portion of the cell culture; wherein about 90% of the components have a size smaller than 1 µm.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) and inactivating agent to inactivate the recombinant viral vector preferably BEI, wherein about 90% of the components i) to iii) have a size smaller than 1 µm. Preferably, BEI is present in concentrations effective to inactivate the baculovirus, preferably in an amount of 2 to about 8 mM BEI, preferably of about 5 mM BEI.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) a neutralization agent to stop the inactivation mediated by the inactivating agent, wherein about 90% of the components i) to iii) have a size smaller than 1 µm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In a preferred embodiment, the immunogenic composition comprises PCV2 ORF-2 protein as provided herewith, preferably in concentrations described above, which is mixed with an adjuvant, preferably Carbopol, and physiological saline.

Those of skill in the art will understand that the composition used herein may incorporate known injectable, physiologically acceptable sterile solutions. For preparing a ready-to-use solution for parenteral injection or infusion, aqueous isotonic solutions, such as e.g. saline or corresponding plasma protein solutions, are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethyl-endiamintetracetic acid, among others.

"Adjuvants" as used herein, can include aluminium hydroxide and aluminium phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). JohnWiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol, in particular the use of Carbopol 971P, preferably in amounts of about 500 µg to about 5 mg per dose, even more preferred in an amount of about 750 µg to about 2.5 mg per dose and most preferred in an amount of about 1 mg per dose.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314, or muramyl dipeptide among many others.

Preferably, the adjuvant is added in an amount of about 100 µg to about 10 mg per dose. Even more preferably, the adjuvant is added in an amount of about 100 µg to about 10 mg per dose. Even more preferably, the adjuvant is added in an amount of about 500 µg to about 5 mg per dose. Even more preferably, the adjuvant is added in an amount of about 750 µg to about 2.5 mg per dose. Most preferably, the adjuvant is added in an amount of about 1 mg per dose.

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferably, the composition provided herewith, contains PCV2 ORF-2 protein recovered from the supernatant of in vitro cultured cells, wherein said cells were infected with a recombinant viral vector containing PCV2 ORF-2 DNA and expressing PCV2 ORF-2 protein, and wherein said cell culture was treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM.

According to a further embodiment, the present invention also relates to the use of PCV2 antigen for the preparation of a immunogenic composition for the reduction of concomitant infections caused by one or more pathogens other than PCV-2 in pigs or a herd of pigs, wherein said immunogenic composition comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to iii) have a size smaller than 1 µm. Preferably, said pigs are co-infected with PCV2 as defined above, exposed to PCV2, or endangered or susceptible to get infected with PCV2. More preferred, the number of pigs infected with said pathogens other than circovirus, is reduced with regard to one or more of said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

The immunogenic composition as used herein also refers to a composition that comprises per one ml i) at least 1.6 µg of PCV2 ORF-2 protein described above, ii) at least a portion of baculovirus expressing said PCV2 ORF-2 protein iii) a portion of the cell culture, iv) about 2 to 8 mM BEI, v) sodium thiosulfate in equivalent amounts to BEI; and vi) about 1 mg Carbopol 971, and vii) phosphate salt in a physiologically acceptable concentration; wherein about 90% of the components i) to iii) have a size smaller than 1 µm and the pH of said immunogenic composition is adjusted to about 6.5 to 7.5.

The immunogenic compositions can further include one or more other immuno-modulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 250 µg/ml dose of the vaccine composition. Thus, the immunogenic composition as used herein also refers to a composition that comprises from about 1 ug/ml to about 60 µg/ml of antibiotics, and more preferably less than about 30 µg/ml of antibiotics.

The immunogenic composition as used herein also refers to a composition that comprises i) any of the PCV2 ORF-2 proteins described above, preferably in concentrations described above, ii) at least a portion of the viral vector expressing said PCV2 ORF-2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol 971 in amounts described above; vii) a pharmaceutical acceptable concentration of a saline buffer, preferably of a phosphate salt, and viii) an anti-microbiological active agent; wherein about 90% of the components i) to iii) have a size smaller than 1 µm.

The immunogenic composition as used herein also refers to Ingelvac® CircoFLEX™, (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA). Thus according to another aspect, the present invention relates to a method for reducing the percentage of concomitant infections in pigs or a herd of pigs caused by one or more pathogens other than PCV2 comprising the step administering to said pig(s) an effective amount of PCV2 antigen or an immunogenic composition comprising PCV2 antigen, wherein said immunogenic composition comprising a PCV2 antigen is Ingelvac® CircoFLEX™, CircoVac®, CircoVent and/or Suvaxyn PCV-2 One Dose®, preferably it is Ingelvac® CircoFLEX™. Preferably, said infected pigs are co-infected with PCV2 as defined above, exposed to PCV2, or endangered or susceptible to get infected with PCV2. More preferred, the number of pigs infected with said pathogens other than circovirus, is reduced with regard to one or more of said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group.

The term "an effective amount of PCV2 antigen" as used herein means but is not limited to an amount of PCV2 antigen, that elicits or is able to elicit an immune response in an animal, to which said effective amount of PCV2 antigen is administered.

The amount that is effective depends on the ingredients of the vaccine and the schedule of administration. Typically, when an inactivated virus or a modified live virus preparation is used in the combination vaccine, an amount of the vaccine containing about $10^{2.0}$ to about $10^{9.0}$ TCID$_{50}$ per dose, preferably about $10^{3.0}$ to about $10^{8.0}$ TCID$_{50}$ per dose, more preferably, about $10^{4.0}$ to about $10^{8.0}$ TCID$_{50}$ per dose. In particular, when modified live PCV2 is used in the vaccines, the recommended dose to be administered to the susceptible animal is preferably about $10^{3.0}$ TCID$_{50}$ (tissue culture infective dose 50% end point)/dose to about $10^{6.0}$ TCID$_{50}$/dose and more preferably about $10^{4.0}$ TCID$_{50}$/dose to about $10^{5.0}$ TCID$_{50}$/dose. In general, the quantity of antigen will be between 0.2 and 5000 micrograms, and between $10^{2.0}$ and $10^{9.0}$ TCID$_{50}$, preferably between $10^{3.0}$ and $10^{6.0}$ TCID$_{50}$, more preferably between $10^{4.0}$ and $10^{5.0}$ TCID$_{50}$, when purified antigen is used.

Sub-unit vaccines are normally administered with an antigen inclusion level of at least 0.2 µg antigen per dose, preferably with about 0.2 to about 400 µg/dose, still more preferably with about 0.3 to about 200 µg/dose, even more preferably with about 0.35 to about 100 µg/dose, still more preferably with about 0.4 to about 50 µg/dose, still more preferably with about 0.45 to about 30 µg/dose, still more preferably with about 0.6 to about 16 µg/dose, even more preferably with about 0.75 to about 8 µg/dose, even more preferably with about 1.0 to about 6 µg/dose, still more preferably with about 1.3 to about 3.0 µg/dose.

The administration of PCV2 antigen to pigs does not only result in the reduction the percentage of concomitant infections caused by pathogens other than circovirus, in particular other than PCV2, but also to a general improvement of health, particularly to the resistance against such concomitant infections. Thus, according to another aspect, the present invention also relates to a method for improving the resistance of pigs against one or more concomitant infections with pathogens other than PCV2, comprising the step administering to said pig(s) an effective amount of PCV2 antigen or an immunogenic composition comprising PCV2 antigen. Preferably, said pigs are co-infected with PCV2 as defined above, exposed to PCV2, or endangered or susceptible to get infected with PCV2.

The term "improving the resistance of pigs against concomitant infections" as used herein refers but is not limited to a process wherein the number of pigs infected with a pathogen other than circovirus, is reduced with regard to said pathogen for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. Thus, according to another aspect, the present invention also relates to a method for improving the resistance of pigs against concomitant infections with one or more pathogens other than PCV2, comprising the step administering to said pig(s) an effective amount of PCV2 antigen or an immunogenic composition comprising PCV2 antigen, wherein the number of pigs infected with one or more of said pathogens other than circovirus, is reduced with regard to one or more of said pathogens for more than 10%, preferably for more than 20%, more preferred for more than 30%, even more preferred for more than 40%, even more preferred for more than 50%, even more preferred for more than 60%, even more preferred for more than 80% even more preferred for more than 100% as compared to a non-vaccinated control group. Preferably, said pigs are co-infected with PCV2 as defined above, exposed to PCV2, or endangered or susceptible to get infected with PCV2.

DETAILED DESCRIPTION OF THE PREFERRED EMBODIMENTS

The following examples set forth preferred materials and procedures in accordance with the present invention. Although any methods and materials similar or equivalent to those described herein can be used in the practice or testing of the present invention, the preferred methods, devices, and materials are now described. It is to be understood, however, that these examples are provided by way of illustration only, and nothing therein should be deemed a limitation upon the overall scope of the invention.

EXAMPLE 1

Detection of Concomitant Infections in PCV-2 Infected Animals

Study Population

The study was conducted in the Southern part of Germany. Hybrid pigs of commercial cross breeds (Landrace or Edelschwein (f)×Pietrain (m)) were obtained from 15 different breeding farms being part of a "pig-producer community". The breeding farms differed in size (50 to 300 sows), management and health status. Routine preventive measures of the piglets on all breeding farms included iron injection, tooth and tail cutting and castration. Following weaning at the age of approximately 4 weeks piglets of the different breeding farms were transferred to a nursery farm with an all-in-all-out production system. They were housed commingled in three barns with pens designed to hold 60 to 120 pigs per pen. Routine preventive measures at the nursery site included prophylactic treatment with tetracyclinhydrochlorid for the first ten days after arrival. Four changes of food composition were performed during nursery. The feed provided to the animals was self-prepared based on barely and minerals. At the age of approximately 12 weeks pigs were transferred to a fattening farm with an all-in-all-out production system. They were newly commingled and housed in two stables with pens designed to hold 10 to 30 pigs per pen. Three changes of food composition were performed during fattening. The feed provided was self-prepared based on barely, wheat, corn, and whey concentrate. Pigs remained at the fattening farm for 13 to 18 weeks.

Disease History

The disease pattern of PMWS had become clinically apparent approximately three years prior to study initiation in November 2002 and was serologically confirmed in December 2002. At the end of nursery/beginning of fattening animals started to show typical signs of PMWS such as wasting, respiratory signs and a marked increase in the mortality rate. The disease was complicated by co-infections with PRRSV. Mortality rate during nursery (4-12 weeks of age) usually ranged between 3.5 and 4.8% but peak levels of up to 10% mortality were also occasionally reported. During the middle to late phase of fattening respiratory signs and growth retardation were predominating in PCV2 infected animals. Mortality rate during fattening (12-26 week old pigs) was approximately 1.7-2.4% and the number of culls was 1%. Average daily weight gain was only moderate (719-731 g/day). Three months before study initiation, the diagnosis of PMWS was verified on the basis of clinical signs and PCV2 viraemia that both occurred when animals were approximately 9 to 13 weeks old. PRRSV and *Mycoplasma hyorhinis* were identified in lung lavage samples of PCV2 infected animals as coinfecting pathogens.

Test Articles

For active vaccination against PCV2, an inactivated sub-unit vaccine (Ingelvac® CircoFLEX™, Boehringer Ingelheim Vetmedica GmbH) was administered. The vaccine contained the ORF2 capsid protein of PCV2 as active component and carbomer as adjuvant. The ORF2 sequence was derived from a North American PCV2 isolate that was isolated from tonsil and liver samples of two pigs with signs of PMWS. The ORF2 sequence was subsequently inserted into a baculovirus expression system using an insect cell line derived from ovaries of the armyworm Sodoptera frugiperda (SF+ cells) as host. As control article served a placebo containing PCV2 capsid protein-free cell culture supernatant and carbomer as adjuvant.

Experimental Design

The field trial was performed according to the principles of "Good Clinical Practice" (GCP) and followed a randomized, negative-controlled, double-blinded, parallel study design. A total of 1519 healthy piglets were equally distributed among two treatment groups with regard to initial body weight and litter assignment. One week before weaning, one group of piglets (n=754) was vaccinated with Ingelvac® CircoFLEX™ and the other group (n=765) received a placebo. The test articles were administered as a single 1 ml dose intramuscularly in the right neck region when piglets were 25.4±3.18 days (mean±S.D.) old. After weaning pigs of both treatment groups were kept in mixed groups until the end of finishing in order to maximise the uniform exposure to pathogens.

Polymerase Chain Reactions

Polymerase chain reaction assays were used as described in order to detect specific nucleic acids for PRRSV (Mardassi H, et al., J Clin Microbiol 1994; 32(9):2197-203), *Mycoplasma hyorhinis* (Caron J., et al., J Clin Microbiol 2000; 38(4):1390-6), *Mycoplasma hyopneumoniae* (Calsamiglia M, et al., J Vet Diagn Invest 1999 May; 11(3):246-51), *Streptococcus suis* (Wisselink H J, et al., J Clin Microbiol 2002 August; 40(8):2922-9), *Pasteurella multocida* (Townsend K M, et al., J Clin Microbiol 1998 April; 36(4):1096-100), *Actinobacillus pleuropneumoniae* (Schaller A, et al., Apx toxins in Pasteurellaceae species from animals. Vet Microbiol 2000 Jun. 12; 74(4):365-76), *Bordetella bronchispectica* (Hozbor D, et al., Res Microbiol 1999 June; 150(5):333-41) and *Haemophilus parasuis* (Calsamiglia M, et al., J Vet Diagn Invest 1999 March; 11(2):140-5) in lung tissue samples.

For quantification of the PCV2 viral load in serum, PCV2 genome equivalents was/is quantified according to the method described in Brunborg et al., 2004; J. Virol Methods 122: 171-178. For amplification of PCV2, primers PCV2-84-1265U21 and PCV2-84-1319L21 were/are used. The cut-off level for a positive sample was set as $10^4$ template copies per ml serum based on validation experiments. All PCV2 DNA quantification assays were performed by bioScreen GmbH, Minster, Germany.

Results

PCV2 Viraemia

It was investigated whether the onset and severity of the observed PMWS characteristic clinical signs and lesions were related to the onset of PCV2 viraemia in the blood of pre-selected "sample animals". As illustrated in FIG. 1, the onset of PCV2 viraemia started in the placebo-treated group when animals were approximately 9-10 weeks old. Peak levels with up to 85% PCV2 positive animals were reached when animals were approximately 11 to 14 weeks old. From 14 weeks of age until the end of fattening, the proportion of PCV2 viraemic animals was decreasing without however reaching baseline levels again. In the average the individual duration of viraemia lasted for 56 days (data not shown).

Figure 1B:
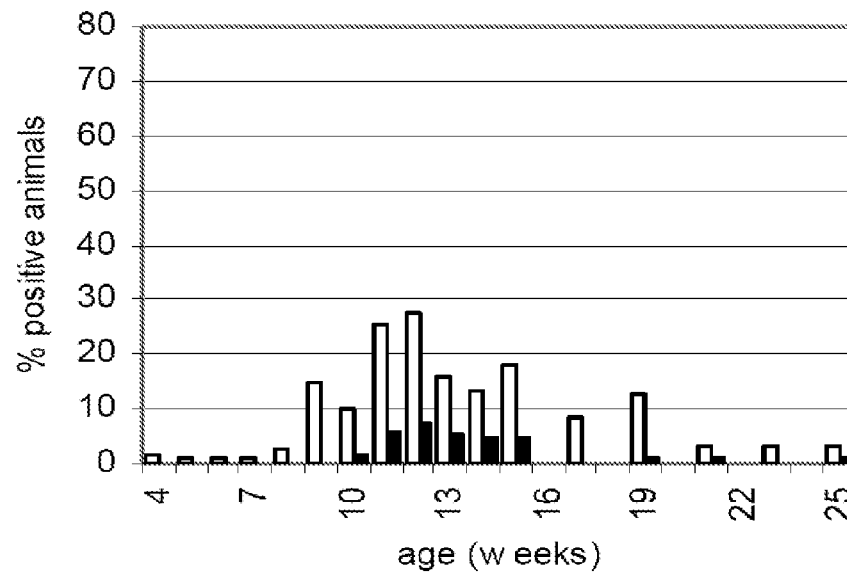
FIG. 1B is a profile of PCV2 viraemia. Blood samples from 110 pre-selected vaccinated animals were collected at the indicated time points. On the basis of the quantitative PCR results animals were grouped into classes of animals with sub-clinical viral loads ($10^4$-$10^6$ gE/ml) and clinical relevant viral loads (>$10^6$ gE/ml). White bars represent the proportion of animals with subclinical viral loads and black bars illustrate the proportion of animals with clinical relevant viral loads per sampling day.

Compared to the placebo-treated group the proportion of PCV2 positive animals in the vaccinated group was significantly reduced (p<0.0001) with no more than 35% of positive animals at the peak of viraemia (FIG. 1B). The average duration of viraemia in vaccinated animals was reduced by 31 days (p<0.0001; data not shown).

Another focus was placed on the examination of the viral load in animals. In this study viral loads of clinical relevance ($>10^6$ gE/ml of serum) were mainly observed in placebo-treated animals in the early phase of viraemia when animals were approximately 10-15 weeks old (FIG. 1A). At the age of 11 weeks the proportion of animals with clinical relevant viral loads (40%) was higher than the proportion of animals with subclinical relevant viral loads (37%). This ratio was drastically changing at the late phase of viraemia (17-25 weeks of age) due to a significant reduction of infections with clinical relevance. In vaccinated animals that were positive for PCV2, subclinical infections were predominating at all analyzed time points (FIG. 1B).

In summary, the PCV2 profile on the selected study sites during the time of the study were characterized as follows: a) an onset of PCV2 viraemia at study week 9-10 that coincided with the onset of clinical signs and lesions of PMWS, b) a high viral load in placebo-treated animals at the early phase of PCV2 viraemia, c) a significant reduction in the duration of viraemia and in the percentage of animals with clinical and sub-clinical relevant viral loads in vaccinated animals compared to placebo-treated animals.

Presence of Concomitant Infections in Placebo-Treated Animals

The results obtained so far confirm the diagnosis of PMWS within the analyzed study population and indicate that vaccination against PCV2 can considerably protect animals from PMWS. This placebo-controlled immunization experiment therefore allowed the testing of the hypothesis that PMWS causes an underlying immunosuppression in animals. It was speculated that in the case of a PCV2 associated immundeficiency the frequency of co-infections after the onset of PCV2 viraemia would be higher in placebo-treated animals than in the vaccinated animals. In a first step the exposure of the study animals to opportunistic organisms was therefore analyzed in more detail. Since monitoring of clinical signs had shown that animals were predominately affected from respiratory signs it was decided to select lung samples of dead animals for a respective pathogen screening by PCR. In Table 3 results are presented for placebo-treated animals only, since they are considered to reflect most closely natural field conditions.

Before onset of PCV2 viraemia (3-8 weeks of age) the only pathogen that was detected in 2 out of 5 lung samples of placebo-treated animals was *Streptococcus suis*. At onset of PCV2 viraemia (9-10 weeks of age), 1 out of 8 lung samples of placebo-treated animals was found positive for PCV2 while 4 out of 8 analyzed lung samples were tested positive for PRRSV. Other pathogens detected in low numbers either alone or in combination with these two pathogens were *Mycoplasma hyorhinis, Mycoplasma hyopneumoniae* and *Streptococcus suis*. The highest amount of co-infecting pathogens was detected in lung samples of placebo-treated animals during the acute phase of PCV2 viraemia (11-16 weeks of age). Among the 17 lung samples tested positive for PCV2, 12 were also found to be positive for PRRSV and 13 for *Mycoplasma hyorhinis*. In addition, co-infections with *Streptococcus suis* or *Pasteurella multocida* were sporadically detected. Finally, at the late phase of viraemia (17-26 weeks of age) co-infections with *Mycoplasma hyopneumoniae* were predominating (6 out of 7 PCV2 positive lung samples) but co-infections with *Mycoplasma hyorhinis, Actinobacillus pleuropneumoniae* and *Streptococcus suis* were also found. For the entire time period after the onset of viraemia (9-26 weeks of life) only 2 out of 22 of lung samples of placebo-treated animals were tested positive for PCV2 alone. In most analyzed lung samples positive for PCV2 combinations of two or three opportunistic organisms were detected. During the course of the study PCV2 infection was thus seen in association with several respiratory concomitant-infections. The onset and peak of PCV2 viraemia coincided with the onsets and peaks of PRRSV and *Mycoplasma hyorhinis* co-infections whereas the late phase of PCV2 viraemia was accompanied by the onset of a *Mycoplasma hyopneumoniae* infection.

Reduction of Co-Infections by Vaccination Against PCV2

Comparison of the frequency of respiratory pathogens detected in lung samples revealed no major differences among both treatment groups for the time before onset of PCV2 viraemia (data not shown). After the onset of PCV2 viraemia (10-26 weeks of age) the proportion of lung samples of vaccinated animals which were tested positive for *Mycoplasma hyorhinis* and PRRSV was reduced by 71% (p=0.0293) and 46% (p=0.2847), respectively (Table 1).

TABLE 1

Study results of B05 BIVI 030

|  | Placebo | | Vaccine | | reduction |
| --- | --- | --- | --- | --- | --- |
|  | % | (N) | % | (N) | % |
| PCV2 | 92 | (24/26) | 55 | (6/11) | 40 |
| PRRSV | 50 | (13/26) | 27 | (3/11) | 46 |
| M. hyorhinis | 62 | (16/26) | 18 | (2/11) | 71 |
| M. hyopneumoniae | 23 | (6/26) | 45 | (5/11) | — |
| S. suis | 12 | (3/26) | 27 | (3/11) | — |
| P. multocida | 4 | (1/26) | 9 | (1/11) | — |
| APP | 8 | (2/26) | 0 | (0/11) | 100 |
| B. bronchiseptica | 0 | (0/26) | 0 | (0/11) | 0 |
| H. parasuis | 0 | (0/26) | 0 | (0/11) | 0 |

Furthermore lung samples from placebo-treated animals were sporadically found to be positive for *Actinobacillus pleuropneumoniae*. Slight differences in the number of lung samples positive for *Mycoplasma hyopneumoniae, Streptococcus suis* or *Pasteurella multocida* were observed in a second study among both treatment groups. As indicated in Table 2 these pathogens were either present at only low frequencies (*Streptococcus suis, Pasteurella multocida*) or did appear at the very late phase of PCV2 infection (*Mycoplasma hyopneumoniae*).

In another study (study B05 BIVI 013) a similar resistance to concomitant pathogens was observed in vaccinated animals as presented in Table 2.

TABLE 2

Study results of B05 BIVI 013

|  | Placebo | | Vaccine | | reduction |
| --- | --- | --- | --- | --- | --- |
|  | % | (N) | % | (N) | % |
| P. multocida | 14 | 15/109 | 0 | 0/32 | 100 |
| H. parasuis | 3 | 3/109 | 0 | 0/32 | 100 |
| Salmonella spp. | 5 | 5/109 | 0 | 0/32 | 100 |
| APP | 4 | 4/109 | 0 | 0/32 | 100 |
| S. suis | 50 | 15/30 | n.a. | n.a. | n.a. |

Under the influence of vaccination against PCV-2 the frequency of PCV2 infections as well as the frequency of *Actinobacillus pleuropneumoniae, Haemophilus parasuis, Mycoplasma hyrhinis, Pasteurella multocida*, PRRSV, *Salmonella* spp., *Strepococcus suis*. co-infections was thus notably reduced.

In another study a similar resistance to *Mycoplasma hypopneumoniae* was observed in vaccinated animals also.

LITERATURE

[1] Clark T. Pathology of the Postweaning Multisystemic Wasting Syndrome of Pigs. 1996 p. 22-5.

[2] Brunborg I M, Moldal T, Jonassen C M. Quantitation of porcine circovirus type 2 isolated from serum/plasma and tissue samples of healthy pigs and pigs with postweaning multisystemic wasting syndrome using a TaqMan-based real-time PCR. J Virol Methods 2004 Dec. 15; 122(2):171-8.

[3] Allan G, McNeilly F. PMWS/PCVD: Diagnosis, Disease and Control: What do we know? 2006 Jul. 16-2006 Jul. 19; 2006.

[4] Allan G M, McNeilly F, Ellis J, et al. PMWS: experimental model and co-infections. Vet Microbiol 2004 Feb. 4; 98(2): 165-8.

[5] Chae C. Postweaning multisystemic wasting syndrome: a review of aetiology, diagnosis and pathology. Vet J 2004 July; 168(1):41-9.

[6] Chae C. A review of porcine circovirus 2-associated syndromes and diseases. Vet J 2005 May; 169(3):326-36.

[7] Segales J, Domingo M, Chianini F, et al Immunosuppression in postweaning multisystemic wasting syndrome affected pigs. Vet Microbiol 2004 Feb. 4; 98(2):151-8.

[8] Krakowka S, Ellis J A, McNeilly F, Ringler S, Rings D M, Allan G. Activation of the immune system is the pivotal event in the production of wasting disease in pigs infected with porcine circovirus-2 (PCV-2). Vet Pathol 2001 January; 38(1):31-42.

[9] Allan G M, Kennedy S, McNeilly F, et al. Experimental reproduction of severe wasting disease by co-infection of pigs with porcine circovirus and porcine parvovirus. J Comp Pathol 1999 July; 121(1):1-11.

[10] Allan G M, McNeilly F, Ellis J, et al. Experimental infection of colostrum deprived piglets with porcine circovirus 2 (PCV2) and porcine reproductive and respiratory syndrome virus (PRRSV) potentiates PCV2 replication. Arch Virol 2000; 145(11):2421-9.

[11] Harms P A, Sorden S D, Halbur P G, et al. Experimental reproduction of severe disease in CD/CD pigs concurrently infected with type 2 porcine circovirus and porcine reproductive and respiratory syndrome virus. Vet Pathol 2001 September; 38(5):528-39.

[12] Krakowka S, Ellis J A, Meehan B, Kennedy S, McNeilly F, Allan G. Viral wasting syndrome of swine: experimental reproduction of postweaning multisystemic wasting syndrome in gnotobiotic swine by coinfection with porcine circovirus 2 and porcine parvovirus. Vet Pathol 2000 May; 37(3):254-63.

[13] Ostanello F, Caprioli A, Di F A, et al. Experimental infection of 3-week-old conventional colostrum-fed pigs with porcine circovirus type 2 and porcine parvovirus. Vet Microbiol 2005 Jul. 1; 108(3-4):179-86.

[14] Rovira A, Balasch M, Segales J, et al. Experimental inoculation of conventional pigs with porcine reproductive and respiratory syndrome virus and porcine circovirus 2. J Virol 2002 April; 76(7):3232-9.

[15] Darwich L, Segales J, Mateu E. Pathogenesis of postweaning multisystemic wasting syndrome caused by Porcine circovirus 2: An immune riddle. Arch Virol 2004 May; 149(5):857-74.

[16] Krakowka S, Ellis J A, McNeilly F, et al Immunologic features of porcine circovirus type 2 infection. Viral Immunol 2002; 15(4):567-82.

[17] Batista L. Postweaning Multisystemic Wasting Syndrom (PMWS) in Quebec, is it an emerging disease? 2006 Mar. 4-2006 Mar. 7; 2006.

[18] Blanchard P, Mahe D, Cariolet R, et al. Protection of swine against post-weaning multisystemic wasting syndrome (PMWS) by porcine circovirus type 2 (PCV2) proteins. Vaccine 2003 Nov. 7; 21(31):4565-75.

[19] Caron J., Ouardani M., Dea S. Diagnosis and differentiation of *Mycoplasma hyopneumoniae* and *Mycoplasma hyorhinis* infections in pigs by PCR amplification of the p36 and p46 genes. J Clin Microbiol 2000; 38(4):1390-6.
[20] Calsamiglia M, Pijoan C, Trigo A. Application of a nested polymerase chain reaction assay to detect *Mycoplasma hyopneumoniae* from nasal swabs. J Vet Diagn Invest 1999 May; 11(3):246-51.
[21] Wisselink H J, Joosten J J, Smith H E. Multiplex PCR assays for simultaneous detection of six major serotypes and two virulence-associated phenotypes of *Streptococcus suis* in tonsillar specimens from pigs. J Clin Microbiol 2002 August; 40(8):2922-9.
[22] Townsend K M, Frost A J, Lee C W, Papadimitriou J M, Dawkins H J. Development of PCR assays for species- and type-specific identification of *Pasteurella multocida* isolates. J Clin Microbiol 1998 April; 36(4):1096-100.
[23] Schaller A, Kuhnert P, de la Puente-Redondo V A, Nicolet J, Frey J. Apx toxins in Pasteurellaceae species from animals. Vet Microbiol 2000 Jun. 12; 74(4):365-76.
[24 Hozbor D, Fouque F, Guiso N. Detection of *Bordetella bronchiseptica* by the polymerase chain reaction. Res Microbiol 1999 June; 150(5):333-41.
[25] Calsamiglia M, Pijoan C, Solano G, Rapp-Gabrielson V. Development of an oligonucleotide-specific capture plate hybridization assay for detection of *Haemophilus*

The invention claimed is:

1. A method for reducing the percentage of concomitant infections in pigs or a herd of pigs caused by one or more pathogens other than PCV2 comprising the step administering to said pig(s) a single dose of an immunogenic composition comprising 4-400 µg of PCV2 ORF2 antigen and at least one further component selected from the group consisting of inactivated viral vector, cell culture supernate, media, viral inactivators, neutralization agents for viral inactivators, antibiotics, and combinations thereof, wherein the number of pigs infected with one or more of the pathogens other than PCV2 is reduced with regard to one or more of the pathogens by more than 10% after a single dose of the immunogenic composition comprising PCV2 ORF2 when compared to those pigs not receiving the PCV2 ORF2 composition, and wherein the concomitant infections are selected from the group of consisting of *Actinobacillus pleuropneumoniae, Haemophilus parasuis, Mycoplasma hyrhinis, Mycoplasma hyopneumoniae, Pasteurella multocida, Salmonella* spp., *Streptococcus suis*, porcine reproductive and respiratory syndrome virus (PRRSV), and combinations thereof.

2. The method according to claim 1, characterized in that the pigs or the herd of pigs are/is infected with PCV2.

3. A method for improving the resistance of pigs against concomitant infections with one or more pathogens other than PCV2, comprising the step administering to said pig(s) a single dose of an immunogenic composition comprising 4-400 μg of PCV2 ORF2 antigen and at least one further component selected from the group consisting of inactivated viral vector, cell culture supernate, media, viral inactivators, neutralization agents for viral inactivators, antibiotics, and combinations thereof, wherein the number of pigs infected with one or more of the pathogens other than PCV2 is reduced with regard to one of more of the pathogens by more than 10% after a single dose of the immunogenic composition comprising PCV2 ORF2 when compared to those pigs not receiving the PCV2 ORF2 composition, and wherein the concomitant infections are selected from the group consisting of *Actinobacillus pleuropneumoniae, Haemophilus parasuis, Mycoplasma hyrhinis, Mycoplasma hyopneumoniae, Pasteurella multocida, Salmonella* spp., *Strepococcus suis*, porcine reproductive and respiratory syndrome virus (PRRSV), and combinations thereof.

4. The method according to claim 3, characterized in that the pigs are infected with PCV2.

* * * * *

SEQUENCE LISTING

```
<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence.

<400> SEQUENCE: 1 ccgccatg                                                                   8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence.

<400> SEQUENCE: 2 gaattc                                                                     6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc         60
ttggccagat cctccgccgc cgcccctggc tcgtccaccc ccgccaccgc taccgttgga        120
gaaggaaaaa tggcatcttc aacacccgcc tctcccgcac cttcggatat actgtggaga        180
aggaaaaatg gcatcttcaa cacccgcctc tcccgcacct tcggatatac tgtgacgact        240
ttgttccccc gggaggggg accaacaaaa tctctatacc ctttgaatac tacagaataa        300
gaaaggttaa ggttgaattc tggccctgct cccccatcac ccagggtgat aggggagtgg        360
gctccactgc tgttattcta gatgataact ttgtaacaaa ggccacagcc taacctatg        420 acccatatgt aaactactcc tcccgccata caatccccca accttctcc taccactccc        480 gttacttcac acccaaacct gttcttgact ccactattga ttacttccaa ccaaataaca        540
aaaggaatca gctttggctg aggctacaaa cctctagaaa tgtggaccac gtaggcctcg        600
gcactgcgtt cgaaaacagt aaatacgacc aggactacaa tatccgtgta accatgtatg        660
tacaattcag agaatttaat cttaaagacc ccccacttaa accctaaatg aat               713

<210> SEQ ID NO 4
<211> LENGTH: 713
<212> TYPE: DNA
```

<213> ORGANISM: Porcine circovirus

<400> SEQUENCE: 4

```
ccgccatgac gtatccaagg aggcgttacc gcagaagaag acaccgcccc cgcagccatc      60
ttggccagat cctccgccgc cgcccctggc tcgtccaccc ccgccaccgc taccgttgga     120
gaaggaaaaa tggcatcttc aacacccgcc tctcccgcac cttcggatat actgtcaagg     180
ctaccacagt cacaacgccc tcctgggcgg tggacatgat gagatttaat attgacgact     240
tgttccccc gggaggggggg accaacaaaa tctctatacc ctttgaatac tacagaataa     300
gaaaggttaa ggttgaattc tggccctgct cccccatcac ccagggtgat aggggagtgg     360
gctccactgc tgttattcta gatgataact ttgtaacaaa ggccacagcc ctaacctatg     420
acccatatgt aaactactcc tcccgccata caatccccca accttctcc taccactccc     480
gttacttcac acccaaacct gttcttgact ccactattga ttacttccaa ccaaataaca     540
aaaggaatca gctttggctg aggctacaaa cctctagaaa tgtggaccac gtaggcctcg     600
gcactgcgtt cgaaaacagt aaatacgacc aggactacaa tatccgtgta accatgtatg     660
tacaattcag agaatttaat cttaaagacc ccccacttga accctaagaa ttc             713
```

<210> SEQ ID NO 5
<211> LENGTH: 233
<212> TYPE: PRT
<213> ORGANISM: Porcine circovirus

<400> SEQUENCE: 5

```
Met Thr Tyr Pro Arg Arg Tyr Arg Arg Arg His Arg Pro Arg
  1               5                  10                  15

Ser His Leu Gly Gln Ile Leu Arg Arg Pro Trp Leu Val His Pro
             20                  25                  30

Arg His Arg Tyr Arg Trp Arg Arg Lys Asn Gly Ile Phe Asn Thr Arg
         35                  40                  45

Leu Ser Arg Thr Phe Gly Tyr Thr Val Lys Ala Thr Thr Val Thr Thr
     50                  55                  60

Pro Ser Trp Ala Val Asp Met Met Arg Phe Asn Ile Asp Asp Phe Val
 65                  70                  75                  80

Pro Pro Gly Gly Gly Thr Asn Lys Ile Ser Ile Pro Phe Glu Tyr Tyr
                 85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220
```

```
Asn Leu Lys Asp Pro Pro Leu Lys Pro
225                 230
```

<210> SEQ ID NO 6
<211> LENGTH: 233
<212> TYPE: PRT
<213> ORGANISM: Porcine circovirus

<400> SEQUENCE: 6

```
Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
        20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230
```

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7

```
gcggccgcgg gaattcgatc cgccatgacg tatccaagga ggcgttaccg cagaagaaga      60
caccgccccc gcagccatct tggccagatc ctccgccgcc gccccctggct cgtccacccc    120 cgccaccgct accgttggag aaggaaaaat ggcatcttca acacccgcct ctcccgcacc    180
ttcggatata ctgtcaaggc taccacagtc acaacgccct cctgggcggt ggacatgatg    240
agatttaata ttgacgactt tgttccccg ggagggggga ccaacaaaat ctctataccc    300
tttgaatact acagaataag aaaggttaag gttgaattct ggccctgctc ccccatcacc    360
```

```
cagggtgata ggggagtggg ctccactgct gttattctag atgataactt tgtaacaaag    420
gccacagccc taacctatga cccatatgta aactactcct cccgccatac aatccccaa     480 cccttctcct accactcccg ttacttcaca cccaaacctg ttcttgactc cactattgat    540
tacttccaac caaataacaa aaggaatcag ctttggctga ggctacaaac ctctagaaat    600
gtggaccacg taggcctcgg cactgcgttc gaaaacagta aatacgacca ggactacaat    660
atccgtgtaa ccatgtatgt acaattcaga gaatttaatc ttaaagaccc ccccacttgaa   720 ccctaagaat tctatcacta gtgaattcgc ggccgc                              756
```

<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2, ORF-2construct, which includes baculovirus and pGEM T-easy coding sequences.

<400> SEQUENCE: 8

```
aagctttact cgtaaagcga gttgaaggat catatttagt tgcgtttatg agataagatt     60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
gtgactagcg aagaagatgt gtggaccgca gaacagatag taaaacaaaa ccctagtatt    240
ggagcaataa tcgatttaac caacacgtct aaatattatg atggtgtgca tttttttgcgg   300 gcgggcctgt tatacaaaaa aattcaagta cctggccaga ctttgccgcc tgaaagcata    360
gttcaagaat ttattgacac ggtaaaagaa tttacagaaa agtgtcccgg catgttggtg    420
ggcgtgcact gcacacacgg tattaatcgc accggttaca tggtgtgcag atatttaatg    480
cacaccctgg gtattgcgcc gcaggaagcc atagatagat tcgaaaaagc cagaggtcac    540
aaaattgaaa gacaaaatta cgttcaagat ttattaattt aattaatatt atttgcattc    600
tttaacaaat actttatcct attttcaaat tgttgcgctt cttccagcga accaaaacta    660
tgcttcgctt gctccgttta gcttgtagcc gatcagtggc gttgttccaa tcgacggtag    720
gattaggccg gatattctcc accacaatgt tggcaacgtt gatgttacgt ttatgctttt    780
ggttttccac gtacgtcttt tggccggtaa tagccgtaaa cgtagtgccg tcgcgcgtca    840
cgcacaacac cggatgtttg cgcttgtccg cggggtattg aaccgcgcga tccgacaaat    900
ccaccacttt ggcaactaaa tcggtgacct gcgcgtcttt tttctgcatt atttcgtctt    960
tcttttgcat ggtttcctgg aagccggtgt acatgcggtt tagatcagtc atgacgcgcg   1020
tgacctgcaa atctttggcc tcgatctgct tgtccttgat ggcaacgatg cgttcaataa   1080
actcttgttt tttaacaagt tcctcggttt tttgcgccac caccgcttgc agcgcgtttg   1140
tgtgctcggt gaatgtcgca atcagcttag tcaccaactg tttgctctcc tcctcccgtt   1200
gtttgatcgc gggatcgtac ttgccggtgc agagcacttg aggaattact tcttctaaaa   1260
gccattcttg taattctatg gcgtaaggca atttggactt cataatcagc tgaatcacgc   1320
cggatttagt aatgagcact gtatgcggct gcaaatacag cgggtcgccc cttttcacga   1380
cgctgttaga ggtagggccc ccattttgga tggtctgctc aaataacgat ttgtatttat   1440
tgtctacatg aacacgtata gctttatcac aaactgtata ttttaaactg ttagcgacgt   1500
ccttggccac gaaccggacc tgttggtcgc gctctagcac gtaccgcagg ttgaacgtat   1560
```

```
cttctccaaa tttaaattct ccaattttaa cgcgagccat tttgatacac gtgtgtcgat    1620
tttgcaacaa ctattgtttt ttaacgcaaa ctaaacttat tgtggtaagc aataattaaa    1680
tatgggggaa catgcgccgc tacaacactc gtcgttatga acgcagacgg cgccggtctc    1740
ggcgcaagcg gctaaaacgt gttgcgcgtt caacgcggca acatcgcaa aagccaatag    1800
tacagttttg atttgcatat taacggcgat tttttaaatt atcttattta ataaatagtt    1860
atgacgccta caactcccg cccgcgttga ctcgctgcac ctcgagcagt tcgttgacgc    1920
cttcctccgt gtggccgaac acgtcgagcg ggtggtcgat gaccagcggc gtgccgcacg    1980
cgacgcacaa gtatctgtac accgaatgat cgtcgggcga aggcacgtcg gcctccaagt    2040
ggcaatattg gcaaattcga aaatatatac agttgggttg tttgcgcata tctatcgtgg    2100
cgttgggcat gtacgtccga acgttgattt gcatgcaagc cgaaattaaa tcattgcgat    2160
tagtgcgatt aaaacgttgt acatcctcgc ttttaatcat gccgtcgatt aaatcgcgca    2220
atcgagtcaa gtgatcaaag tgtggaataa tgttttcttt gtattcccga gtcaagcgca    2280
gcgcgtattt taacaaacta gccatcttgt aagttagttt catttaatgc aactttatcc    2340
aataatatat tatgtatcgc acgtcaagaa ttaacaatgc gcccgttgtc gcatctcaac    2400
acgactatga tagagatcaa ataaagcgcg aattaaatag cttgcgacgc aacgtgcacg    2460
atctgtgcac gcgttccggc acgagctttg attgtaataa gtttttacga agcgatgaca    2520
tgaccccccgt agtgacaacg atcacgccca aaagaactgc cgactacaaa attaccgagt    2580
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aatgaaaac tgtcgacaag    3240
ctctgtccgt ttgctggcaa ctgcaagggt ctcaatccta tttgtaatta ttgaataata    3300
aaacaattat aaatgctaaa tttgtttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aattttattt tcacataaac    3480
tagacgccct tgtcgtcttct tcttcgtatt ccttctcttt ttcatttttc tcctcataaa    3540
aattaacata gttattatcg tatccatata tgtatctatc gtatagagta aattttttgt    3600
tgtcataaat atatatgtct tttttaatgg ggtgtatagt accgctgcgc atagtttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat tttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
```

```
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
cccgccaccg ctaccgttgg agaaggaaaa atggcatctt caacacccgc tctcccgca    4320 ccttcggata tactgtcaag gctaccacag tcacaacgcc ctcctgggcg gtggacatga    4380
tgagatttaa tattgacgac tttgttcccc cgggaggggg gaccaacaaa atctctatac    4440
cctttgaata ctacagaata agaaaggtta aggttgaatt ctggccctgc tcccccatca    4500
cccagggtga taggggagtg ggctccactg ctgttattct agatgataac tttgtaacaa    4560
aggccacagc cctaacctat gacccatatg taaactactc ctcccgccat acaatccccc    4620
aacccttctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg gccgtccag aattctagaa    4920 ggtacccggg atcctttcct gggacccggc aagaaccaaa aactcactct cttcaaggaa    4980
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcggct gcccaataat gaaccttcac tctgagtaca ccaactcgtt cgaacagttc    5340
atcgatcgtg tcatctggga gaacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtattt    5580 aataattcat taaatttata atctttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactgacg taaacacgtt aaataaagct    5940
tggacatatt aacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacgtc cgcgatcaaa tttgtagttg agcttttgg aattatttct    6120 gattgcgggc gttttgggc gggtttcaat ctaactgtgc ccgatttaa ttcagacaac    6180 acgttagaaa gcgatggtgc aggcggtggt aacatttcag acggcaaatc tactaatggc    6240
ggcggtggtg gagctgatga taaatctacc atcggtggag gcgcaggcgg ggctggcggc    6300
```

```
ggaggcggag gcggaggtgg tggcggtgat gcagacggcg gtttaggctc aaatgtctct    6360
ttaggcaaca cagtcggcac ctcaactatt gtactggttt cgggcgccgt ttttggtttg    6420
accggtctga gacgagtgcg attttttttcg tttctaatag cttccaacaa ttgttgtctg    6480
tcgtctaaag gtgcagcggg ttgaggttcc gtcggcattg gtggagcggg cggcaattca    6540
gacatcgatg gtggtggtgg tggtggaggc gctggaatgt taggcacggg agaaggtggt    6600
ggcggcggtg ccgccggtat aatttgttct ggtttagttt gttcgcgcac gattgtgggc    6660
accggcgcag gcgccgctgg ctgcacaacg gaaggtcgtc tgcttcgagg cagcgcttgg    6720
ggtggtggca attcaatatt ataattggaa tacaaatcgt aaaaatctgc tataagcatt    6780
gtaatttcgc tatcgtttac cgtgccgata tttaacaacc gctcaatgta agcaattgta    6840
ttgtaaagag attgtctcaa gctcgccgca cgccgataac aagccttttc atttttacta    6900
cagcattgta gtggcgagac acttcgctgt cgtcgacgta catgtatgct ttgttgtcaa    6960
aaacgtcgtt ggcaagcttt aaatatttta aagaacatc tctgttcagc accactgtgt    7020
tgtcgtaaat gttgtttttg ataatttgcg cttccgcagt atcgacacgt tcaaaaaatt    7080
gatgcgcatc aattttgttg ttcctattat tgaataaata agattgtaca gattcatatc    7140
tacgattcgt catggccacc acaaatgcta cgctgcaaac gctggtacaa ttttacgaaa    7200
actgcaaaaa cgtcaaaact cggtataaaa taatcaacgg gcgctttggc aaaatatcta    7260
ttttatcgca caagcccact agcaaattgt atttgcagaa aacaatttcg gcgcacaatt    7320
ttaacgctga cgaaataaaa gttcaccagt taatgagcga ccacccaaat tttataaaaa    7380
tctatttttaa tcacggttcc atcaacaacc aagtgatcgt gatggactac attgactgtc    7440
ccgatttatt tgaaacacta caaattaaag gcgagctttc gtaccaactt gttagcaata    7500
ttattagaca gctgtgtgaa gcgctcaacg atttgcacaa gcacaatttc atacacaacg    7560
acataaaact cgaaaatgtc ttatatttcg aagcacttga tcgcgtgtat gtttgcgatt    7620
acggattgtg caaacacgaa aactcactta gcgtgcacga cggcacgttg gagtatttta    7680
gtccggaaaa aattcgacac acaactatgc acgtttcgtt tgactggtac gcggcgtgtt    7740
aacatacaag ttgctaacgt aatcatggtc atagctgttt cctgtgtgaa attgttatcc    7800
gctcacaatt ccacacaaca tacgagccgg aagcataaag tgtaaagcct ggggtgccta    7860
atgagtgagc taactcacat taattgcgtt gcgctcactg cccgctttcc agtcgggaaa    7920
cctgtcgtgc cagctgcatt aatgaatcgg ccaacgcgcg gggagaggcg gtttgcgtat    7980
tgggcgctct tccgcttcct cgctcactga ctcgctgcgc tcggtcgttc ggctgcggcg    8040
agcggtatca gctcactcaa aggcggtaat acggttatcc acagaatcag gggataacgc    8100
aggaaagaac atgtgagcaa aaggccagca aaaggccagg aaccgtaaaa aggccgcgtt    8160
gctggcgttt ttccataggc tccgcccccc tgacgagcat cacaaaaatc gacgctcaag    8220
tcagaggtgg cgaaacccga caggactata aagataccag gcgtttcccc ctggaagctc    8280
cctcgtgcgc tctcctgttc cgaccctgcc gcttaccgga tacctgtccg cctttctccc    8340
ttcgggaagc gtggcgcttt ctcatagctc acgctgtagg tatctcagtt cggtgtaggt    8400
cgttcgctcc aagctgggct gtgtgcacga accccccgtt cagcccgacc gctgcgcctt    8460
atccggtaac tatcgtcttg agtccaaccc ggtaagacac gacttatcgc cactggcagc    8520
agccactggt aacaggatta gcagagcgag gtatgtaggc ggtgctacag agttcttgaa    8580
gtggtggcct aactacggct acactagaag gacagtattt ggtatctgcg ctctgctgaa    8640
gccagttacc ttcggaaaaa gagttggtag ctcttgatcc ggcaaacaaa ccaccgctgg    8700
```

-continued

```
tagcggtggt ttttttgttt gcaagcagca gattacgcgc agaaaaaaag gatctcaaga      8760
agatcctttg atcttttcta cggggtctga cgctcagtgg aacgaaaact cacgttaagg      8820
gattttggtc atgagattat caaaaaggat cttcacctag atccttttaa attaaaaatg      8880
aagttttaaa tcaatctaaa gtatatatga gtaaacttgg tctgacagtt accaatgctt      8940
aatcagtgag gcacctatct cagcgatctg tctatttcgt tcatccatag ttgcctgact      9000
ccccgtcgtg tagataacta cgatacggga gggcttacca tctggcccca gtgctgcaat      9060
gataccgcga gacccacgct caccggctcc agatttatca gcaataaacc agccagccgg      9120
aagggccgag cgcagaagtg gtcctgcaac tttatccgcc tccatccagt ctattaattg      9180
ttgccgggaa gctagagtaa gtagttcgcc agttaatagt ttgcgcaacg ttgttgccat      9240
tgctacaggc atcgtggtgt cacgctcgtc gtttggtatg gcttcattca gctccggttc      9300
ccaacgatca aggcgagtta catgatcccc catgttgtgc aaaaaagcgg ttagctcctt      9360
cggtcctccg atcgttgtca gaagtaagtt ggccgcagtg ttatcactca tggttatggc      9420
agcactgcat aattctctta ctgtcatgcc atccgtaaga tgcttttctg tgactggtga      9480
gtactcaacc aagtcattct gagaatagtg tatgcggcga ccgagttgct cttgcccggc      9540
gtcaatacgg gataataccg cgccacatag cagaacttta aaagtgctca tcattggaaa      9600
acgttcttcg gggcgaaaac tctcaaggat cttaccgctg ttgagatcca gttcgatgta      9660
acccactcgt gcacccaact gatcttcagc atctttact ttcaccagcg tttctgggtg      9720
agcaaaaaca ggaaggcaaa atgccgcaaa aaagggaata agggcgacac ggaaatgttg      9780
aatactcata ctcttccttt ttcaatatta ttgaagcatt tatcagggtt attgtctcat      9840
gagcggatac atatttgaat gtatttagaa aaataaacaa ataggggttc gcgcacatt       9900 tccccgaaaa gtgccacctg acgtctaaga accattatt atcatgacat taacctataa      9960
aaataggcgt atcacgaggc cctttcgtct cgcgcgtttc ggtgatgacg gtgaaaacct     10020
ctgacacatg cagctcccgg agacggtcac agcttgtctg taagcggatg ccgggagcag     10080
acaagcccgt cagggcgcgt cagcgggtgt tggcgggtgt cggggctggc ttaactatgc     10140
ggcatcagag cagattgtac tgagagtgca ccatatgcgg tgtgaaatac cgcacagatg     10200
cgtaaggaga aaataccgca tcaggcgcca ttcgccattc aggctgcgca actgttggga     10260
agggcgatcg gtgcgggcct cttcgctatt acgccagctg gcgaaagggg gatgtgctgc     10320
aaggcgatta agttgggtaa cgccagggtt ttcccagtca cgacgttgta aaacgacggc     10380
cagtgcc                                                               10387
```

<210> SEQ ID NO 9
<211> LENGTH: 20
<212> TYPE: PRT
<213> ORGANISM: Porcine circovirus

<400> SEQUENCE: 9

Ser Tyr Pro Arg Arg Arg Tyr Arg Arg Arg Arg His His Pro Pro Ser
1               5                   10                  15

His Leu Gly Gln
            20

<210> SEQ ID NO 10
<211> LENGTH: 19
<212> TYPE: PRT
<213> ORGANISM: Porcine circovirus

```
<400> SEQUENCE: 10

Pro Arg His His Tyr Arg Pro Arg Arg Lys Asn Gly Ile Phe Asn Thr
1               5                   10                  15

Thr Leu Ser

<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine
      circovirus type 2, open reading frame 2.

<400> SEQUENCE: 11

Met Thr Tyr Pro Arg Arg Arg Tyr Arg Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Arg Thr
    50                  55                  60

Pro Ser Trp Ala Val Asp Met Met Arg Phe Asn Ile Asp Asp Phe Val
65                  70                  75                  80

Pro Pro Gly Gly Gly Thr Asn Lys Ile Ser Ile Pro Phe Glu Tyr Tyr
                85                  90                  95

Arg Ile Lys Lys Val Lys Val Glu Phe Trp Pro Cys Ser Pro Ile Thr
            100                 105                 110

Gln Gly Asp Arg Gly Val Gly Ser Thr Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Ile Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Lys Pro
225                 230
```